United States Patent [19]

Kauvar

[11] Patent Number: 5,217,869
[45] Date of Patent: Jun. 8, 1993

[54] METHOD TO PRODUCE IMMUNODIAGNOSTIC REAGENTS

[75] Inventor: Lawrence M. Kauvar, San Francisco, Calif.

[73] Assignee: Terrapin Technologies, Inc., San Francisco, Calif.

[21] Appl. No.: 255,906

[22] Filed: Oct. 11, 1988

Related U.S. Application Data

[63] Continuation-in-part of Ser. No. 108,130, Oct. 13, 1987.

[51] Int. Cl.⁵ .................. G01N 33/543; G01N 33/577
[52] U.S. Cl. .................... 435/7.9; 435/7.93; 435/975; 436/518; 436/548; 436/809; 530/808; 530/809; 530/387.9; 530/388.1; 935/110
[58] Field of Search ........... 435/7.93, 7.9, 975; 436/518, 548, 809; 530/387, 808, 809; 935/110

[56] References Cited

U.S. PATENT DOCUMENTS

| | | | |
|---|---|---|---|
| 4,376,110 | 3/1983 | David | 436/513 |
| 4,427,781 | 1/1984 | Masson | 436/509 |
| 4,443,549 | 4/1984 | Sadowski | 436/548 |
| 4,447,526 | 5/1984 | Rupchock | 435/7 |
| 4,456,691 | 6/1984 | Stark | 436/543 |
| 4,530,786 | 6/1985 | Dunbar | 530/387 |
| 4,554,101 | 11/1985 | Hopp | 436/543 |
| 4,591,570 | 5/1986 | Chang | 436/578 |
| 4,833,092 | 5/1989 | Geysen | 436/501 |
| 4,880,750 | 11/1989 | Francoeur | 436/501 |
| 4,963,263 | 10/1990 | Kauvar | 210/635 |

FOREIGN PATENT DOCUMENTS

| | | |
|---|---|---|
| 8502121 | 5/1985 | World Int. Prop. O. |
| 8600991 | 2/1986 | World Int. Prop. O. |

OTHER PUBLICATIONS

W. D. Huse et al, *Science*, 246, 1275–1281, 1989.
Oldham, *J. Biological Response Modifiers* (1987) 6(3):227–234.
Albert et al., *Report On The Ninth Inter. Histocomp. Workshp. And Conference* (1984) pp. 34, 46, 64–65, 72–74.
Better et al., *Science* (1988) 240:1041–1043.
Carey et al., *Analytical Chem.* (1987) 59:1529–1534.
Casali et al., *Science* (1986) 234:476–479.
Cleary et al., *Cell* (1986) 44:97–106.
Feder, *The New York Times* (Aug. 3, 1988) pp. C4–C5.
Guillet et al., *Science* (1987) 235:865–870.
Levine, *Advances In Cancer Res.* (1982) 37:75–109.
Oldham, *J. Cellular Phys. Supplement* (1986) 4:91–99.
Raychauduri et al., *J. Immunol.* (1986) 137(5):1743–1749.
Skerra et al., *Science* (1988) 240:1038–1040.
Accola et al., *Proc. Natl. Acad. Sci.* (1981) 78:2478–2482.
Berzofski *Science* (1985) 229:932–940.
Gearhart et al., *Proc. Natl. Acad. Sci.* (1983) 80:3439–3443.
Jerne *Ann. Immunol.* (1974) 125:337–389.
Kennedy et al., *Sci. Am.* (1986) 255:48–56.
Lerner, *Nature* (1982) 299:592–596.
Osheroff et al., *J. Immunol.* (1985) 135:306–313.
Owen et al., *Nature* (1982) 295:347–348.
Reading, *J. Immunol. Methods* (1982) 33:R1–R31.
Richards et al., *Science* (1975) 187:130–137.
Rodwell et al., *J. Immunol.* (1983) 130:313–316.
Schreiber et al., *Proc. Natl. Acad. Sci.* (1980) 77:7385–7389.
Schreiber et al., *Proc. Natl. Acad. Sci.* (1981) 78:7535–7539.
Lerner, *Sci. Amer.* (1983) Feb.

*Primary Examiner*—David Saunders
*Attorney, Agent, or Firm*—Morrison & Foerster

[57] ABSTRACT

Screening methods to obtain suitable antibodies for use in immunoassays for analytes not ordinarily susceptible to detection by this means involves in vitro screening of panels of cells secreting a representative selection of antibodies. An application of this method also permits the preparation of specific mimotopes which mimic the immunological activity of the desired analyte, which mimotopes can then be used as competitors in the immunoassay or can be used to immunize subject mammals in order to improve the specificity and affinity of the antibodies. Methods to identify a particular analyte by its pattern of binding strength to a panel of related antibodies and to match an arbitrary analyte with an immunoreactive member of a panel of candidate antibodies are also disclosed.

19 Claims, 11 Drawing Sheets

Acetylate N-terminus on all except E12 (for FITC)

| N-term | 5 | 4 | 3 | C-Term | N-Term | 5 | 4 | 3 | C-Term |
|---|---|---|---|---|---|---|---|---|---|
| 1. V | A | V | F | A | 49. G | S | S | S | F |
| 2. F | G | W | A | I | 50. G | W | G | K | W |
| 3. G | A | V | V | F | 51. W | G | D | G | P |
| 4. V | V | I | A | P | 52. N | S | W | G | A |
| 5. A | A | A | F | F | 53. S | H | P | G | W |
| 6. M | V | V | G | W | 54. S | D | A | A | A |
| 7. I | G | G | V | A | 55. A | N | H | A | A |
| 8. G | F | W | W | M | 56. D | P | W | S | W |
| 9. S | I | P | F | I | 57. W | H | G | P | H |
| 10. W | V | G | W | A | 58. S | G | D | P | V |
| 11. G | P | G | I | F | 59. H | P | H | G | M |
| 12. A | F | V | W | S | 60. S | S | H | A | G |
| 13. N | V | W | P | W | 61. G | P | K | A | A |
| 14. W | I | G | S | W | 62. H | H | G | S | W |
| 15. G | A | G | G | F | 63. A | N | S | S | W |
| 16. G | M | W | G | W | 64. S | M | D | S | W |
| 17. F | V | A | S | G | 65. A | D | A | N | A |
| 18. W | G | A | V | P | 66. G | W | S | D | A |
| 19. A | S | M | I | A | 67. N | H | P | G | G |
| 20. V | A | V | G | S | 68. M | G | K | A | H |
| 21. V | F | S | S | V | 69. N | D | M | S | W |
| 22. M | W | V | H | W | 70. A | N | K | M | G |
| 23. S | V | A | F | P | 71. G | W | S | N | D |
| 24. S | A | M | W | W | 72. G | D | P | D | G |
| 25. A | W | V | G | H | 73. H | A | A | N | D |
| 26. F | W | W | P | H | 74. S | K | S | G | G |
| 27. A | M | S | A | W | 75. D | W | S | W | K |
| 28. W | A | V | P | S | 76. A | D | H | N | G |
| 29. P | G | G | G | W | 77. G | D | S | G | D |
| 30. W | W | S | V | S | 78. S | H | D | P | P |
| 31. V | D | W | A | A | 79. P | S | H | K | M |
| 32. S | G | W | G | M | 80. S | A | G | D | K |
| 33. S | W | H | W | G | 81. D | P | N | A | D |
| 34. M | W | S | G | P | 82. M | H | D | S | P |
| 35. W | A | P | G | S | 83. P | S | D | D | N |
| 36. W | D | W | A | G | 84. D | A | S | D | H |
| 37. A | I | S | P | S | 85. H | D | D | S | S |
| 38. W | S | A | H | W | 86. G | K | M | D | K |
| 39. G | S | G | F | H | 87. D | A | K | S | D |
| 40. A | A | A | S | S | 88. S | S | H | D | K |
| 41. S | S | P | V | A | 89. S | K | F | W | Y |
| 42. G | W | S | G | S | 90. P | L | A | Q | G |
| 43. W | M | H | S | G | 91. P | L | A | Q | G |
| 44. A | S | G | H | W | 92. G | L | A | Q | G |
| 45. N | G | M | G | G | 93. G | L | A | Q | K |
| 46. W | G | N | P | M | 94. S | V | N | M | K |
| 47. P | P | A | S | G | 95. I | A | H | W | D |
| 48. G | H | A | S | A | 96. F | P | K | V | D |

| # | sequences | | | | | | | |
|---|---|---|---|---|---|---|---|---|
| | N TERM | | | | | | | CONH$_2$ |
| 1 | G | I | I | A | A | Y | G | L | Y |
| 2 | G | I | F | A | S | S | S | Y | I |
| 3 | G | F | A | H | A | M | G | T | L |
| 4 | G | A | F | G | W | S | G | S | A |
| 5 | G | L | E | S | A | H | M | W | F |
| 6 | G | A | P | G | T | Y | T | S | A |
| 7 | G | I | I | T | K | A | S | T | T |
| 8 | G | N | Y | S | K | F | W | Y | L |
| 9 | G | L | G | A | A | N | S | K | A |
| 10 | G | A | A | H | E | L | T | S | S |
| 11 | G | N | M | I | T | E | T | D | L |
| 12 | G | E | I | A | H | P | F | D | N |
| 13 | G | S | S | S | I | N | A | K | L |
| 14 | G | G | G | E | T | T | E | M | S |
| 15 | G | K | G | S | N | N | F | F | S |
| 16 | G | F | D | E | T | G | D | W | D |
| 17 | G | D | W | D | G | T | E | D | F |
| 18 | G | S | D | S | H | A | S | D | A |
| 19 | G | K | A | I | T | G | A | R | D |
| 20 | G | F | G | K | K | H | T | D | G |
| 21 | G | T | R | T | M | L | T | R | F |
| 22 | G | A | A | K | S | S | K | H | T |
| 23 | G | R | A | N | G | S | K | N | A |
| 24 | G | A | N | K | S | G | N | A | R |

FIG. 7

METHOD TO PRODUCE IMMUNODIAGNOSTIC REAGENTS

This is a continuation-in-part of U.S. patent application Ser. No. 108,130, filed 13 Oct. 1987.

TECHNICAL FIELD

The invention relates to the use of immunoassay procedures in general, and especially to the use of such procedures in detection and quantitation of materials not normally subject to immunoassay. For example, trace contaminants in water, soil, and air which are normally detected by high performance liquid chromatography may be more conveniently detected by materials produced in the method of the invention.

BACKGROUND ART

The use of immunoassay for detection of a wide range of biological compounds in medical or veterinary context is quite widespread and methods and variations for conducting assays are well known. Recently, in fact, much effort has concentrated on improving the convenience of the assay by redesigning the format. See, for example, U.S. Pat. No. 4,427,781 describing a particle agglutination method which depends on the ability of antibodies to desired small molecular weight haptens to agglutinate particles to which the haptens are attached. Another variation is disclosed in U.S. Pat. No. 4,447,526 which describes an assay where advantage is taken of changes in the properties of a label when a specific binding to the reagent by the hapten to be analyzed occurs. These disclosures are only two of hundreds which describe specific analytical techniques to enhance the convenience or sensitivity of assays that depend on specific interactions between antibody molecules (or fragments of antibodies) with analytes to be detected.

Because of the dependence on this specific interaction, the applicability of an immuno based assay to any particular analyte depends upon the ability to obtain antibodies appropriate for the required specific interaction. There are two aspects to be noted: First, the ability of antibody or fragment thereof to discriminate between the analyte and other materials which may be contaminants in the sample to analyzed must be adequate, i.e., the specificity must be high. Second, the ability of the antibody or fragment to bind tightly to the analyte is also important, i.e., the affinity will determine the sensitivity of the assay. U.S. Pat. No. 4,376,110 to David, for example, discloses use of monoclonal antibodies to improve the affinity properties of the desired interaction.

There are a multitude of analytes which are candidates for detection to which specific and strongly binding antibodies are difficult to raise using standard in vivo techniques. As is well known, the usual procedures for obtaining antibodies to a particular substance involve administering the substance to a suitable subject such as a rat or mouse, and relying on the immune system of the subject to produce B-cells capable of secreting the appropriate antibody. Either polyclonal antisera are obtained for use directly in the assays, if the titers are sufficiently high, and the results are sufficiently satisfactory, or a B-cell source such as the spleen is used to provide fusion partners to obtain hybridomas capable of secreting the desired antibodies. These hybridomas can be screened for production of antibodies specific to the desired analyte. These processes work well if the material is sufficiently large to be immunogenic, sufficiently nontoxic so that the animal is not killed before the antibodies are raised, and sufficiently inexpensive that adequate amounts can be obtained to carry out this procedure. This is not always the case.

The problem of inadequate size can often be solved by conjugating analyte or a modified form thereof to a carrier which provides the required size to confer immunogenicity on what would otherwise be ignored by the immune system as too small. It has been possible to raise antibodies to certain specific molecules in this category by utilizing this now rather conventional technique. For example, U.S. Pat. No. 4,456,691 discloses a process to prepare antibodies reactive with polycholinated biphenyl (PCB) by chemically modifying the PCB and conjugating it to a carrier. A similar procedure is described in U.S. Pat. No. 4,530,786 for the herbicide atrazine. However, such an approach is cumbersome, must be redesigned for every individual analyte, and is not assured of success since the antibodies raised by the conjugate may not in fact be directed to the analyte, but rather to the junction regions between the analyte and the carrier. It is notably more difficult to obtain "neutralizing" antibodies—i.e., those reactive with the analyte itself—by this method.

Whether or nor the problem of toxicity is sufficiently grave to defeat the entire process is, of course, also a matter of chance. With regard to availability of quantities of antigen required, the necessity for minimizing this parameter depends, of course, on the particular antigen.

An analogous problem arises in a therapeutic context. Though still in a developmental stage, the therapeutic procedure of administering monoclonal antibodies immunospecific for a subject's own tumors, with or without the conjugation of label or a toxin, for therapy and/or diagnosis, has achieved some positive results. One approach to acquiring the monoclonal antibodies useful in this context is to isolate the tumor tissue and to use the tissue as an immunogen, followed by preparation and sorting of the derivative monoclonal antibodies using the Kohler and Milstein procedure and an appropriate screen. Clearly this is a cumbersome approach, since several months are required to effect sufficient immunization to allow for construction of the monoclonal antibody panel. By that time, the subject's condition may have deteriorated beyond redemption, or the tumor's antigenic profile may have changed substantially. If a suitable antibody could be selected from a large, already existent, panel, these difficulties could be overcome. A relevant panel for treatment of tumors already exists (Oldham, R. K., *J Biol Resp Mod* (1987) 6:227-234). Additional large panels can also be prepared using recombinant DNA technology. Techniques for screening this panel to obtain a suitable match would be useful in selecting the correct antibody for treatment.

This latter application is representative of the fact that the art offers no general method to obtain an antibody of desired affinity and specificity with regard to any antigen using a generic procedure workable and repeatable for all possible antigens.

The converse problem, i.e., finding a mimotope for a given antibody, has, however, been addressed by Geysen, H. M., PCT application WO86/00991, published 13 Feb. 1986. The word "mimotope", as used hereinbelow, corresponds very roughly to the usage of this term in the Geysen application.

DISCLOSURE OF THE INVENTION

The invention offers methods to produce immunological reagents for any desired analyte, including analytes previously inaccessible to immunoassay, to select an appropriate antibody from an existent set for reaction with a desired target. The various aspects of the processes of the invention all may be, on principle, conducted in vitro, but, in some circumstances, employment of the immunoglobulin somatic diversification system in vivo may be more convenient.

The invention also offers a method to profile a particular analyte by taking advantage of its specific pattern of reactivities against a panel of antibodies of varying specificity. The invention provides novel methods for establishing such profiles by means of a competitive binding assay using competition between a diverse set of mimotopes and the analyte. The invention thereby provides a novel method to obtain mimotopes for a desired analyte. These mimotopes are useful in obtaining increased specificity and affinity in antibodies immunoreactive with the analyte and are also useful as reagents for competitive assays. The invention also provides a method to select an antibody of high specific reactivity for a desired target by screening the target against a reverse image monoclonal antibody panel.

Thus, in one aspect, the invention relates to a method to obtain antibodies reactive with a desired analyte which comprises reacting a panel of randomly generated, immortalized, antibody-producing cells with a mixture of representative mimotopes in competition with the analyte, and then picking the cells producing those antibodies for which the analyte successfully competes. The mimotope panel may vary from random to maximally diverse; maximally diverse panels of mimotopes require fewer members, and are thus advantageous. It is immediately seen that not only has an appropriate antibody or set of antibodies been identified, but a continuous source of that antibody is provided. The antibody thus obtained may at this point, be sufficiently specific and strongly enough binding to provide the desired reagent. This is particularly true in contexts where routine monitoring for a known component in high concentration is the intended application. However, should this not be the case, the invention provides further procedures for optimizing these properties.

In a second aspect, the invention provides a method to obtain a mimotope for a desired analyte which comprises carrying out the above-mentioned procedure and then screening a panel of the mimotopes (generally, those which were contained in the original mixture) for reactivity with the antibody secreted by the cells selected. Those mimotopes which react with the selected antibody thus mimic the analyte with regard to binding to certain immunoglobulins, although not necessarily with respect to toxicity or T-cell recognition as self. Polyclonal antisera reactive with the analyte can then be obtained by administering the mimotopes as substitute immunogens.

This possibility leads to a third aspect of the invention, that is, a method to improve the affinity and specificity of the antibodies originally obtained. Because the mimotope provides a substitute immunogen for analyte, the mimotope can be used to immunize an animal such as rat, mouse, or sheep, and, using conventional immortalization and screening techniques, to obtain the antibodies of desired specificity. This latter in vivo process, while conventional with regard to the procedures to immortalize and screen the resulting B-cell repertoire, is unique in its use of mimotopes whose ability to substitute for analyte is defined by functional tests of homology, rather than chemical structure. These mimotopes are used to immunize the subject and to screen the resulting panel. The analyte itself need not be employed in any of these procedures.

The invention also relates to kits useful in performing the foregoing procedures.

For simplicity, the various procedures which form part of the invention have been described in terms of employing a single mimotope or a single antibody in the screening processes. However, it is further included in the invention, and an improvement on the technique whereby one antibody or one mimotope is employed, to utilize subsets of panels which represent a plurality of successful candidates. In this modification, instead of choosing a single antibody producer from the original group of immortalized antibody-producing cells, a subset of approximately, for example, ten or fifteen such cells is employed. The antibodies produced from this set is then used as a mixture to screen the panel of mimotopes, and, again, rather than selecting a single, most reactive mimotope, a subset, for example, of ten or fifteen, is chosen. This mixture is then used in the immunization procedure, thus letting the immunized organism differentially proliferate B-cells which are responsive to common features of the favored group of mimotopes. The monoclonal panel obtained from immortalizing the B-cell antibody-secreting cells of the immunized animal can then again be screened by competition between the subset pool of mimotopes and the antigen, and the most successful chosen.

In addition to thereby providing a single, highly specific and strongly binding antibody to the analyte, the screen provides a further subset whose pattern of reactivity with regard to the analyte can be preserved and utilized to characterize the presence of the particular analyte of interest, as distinct from imperfectly cross-reactive congeners.

In one application of this concept, a manageable panel of, for example, 25-75 antibodies can be used. A profile of such a panel may be generated by conventional immunoassay technology, or, advantageously, in competition assays between unlabeled, unmodified analyte and labeled mimotope mixtures. The panel can be used for analyte identification or can be used repeatedly to monitor magnitude of the pattern generated by reactivity with a particular analyte as a function of analyte concentration.

Thus, another aspect of the invention relates to utilization of the pattern of reactivity of a specific analyte with regard to a limited panel of antibodies selected from one or several of the random panels. In this aspect, the invention is directed to a panel of antibodies having varying reactivity to a desired analyte, and, optionally, a competition mixture of labeled mimotopes useful to ascertain varying levels of reactivity between analyte and each antibody on the panel in competition with the mimotope mixture. To facilitate generating the desired profiles, a novel method for providing the panel on a solid support is also included in the invention.

Still another aspect of the invention utilizes a maximally diverse set of mimotopes to generate a complementary set of monoclonal antibodies which constitutes an inverse image of the mimotopes. The strict complementarity between these two reference sets, one of mimotopes and the other of antibodies, has additional utility in providing an indexing system that allows small quantities of analyte to be indirectly tested against a large collection of potentially cross-reactive antibodies; the low cost and rapidity of such a preselection method is often of value, for example in the search for antibodies against patient-specific tumor antigens. The invention also relates to procedures for defining a maximally diverse set of mimotopes and to the set so defined.

BRIEF DESCRIPTION OF THE DRAWINGS

FIG. 3 shows a list of diverse mimotopes designed to vary as to hydrophobic index (hi) and hydrophobic moment (hm).

FIG. 7 shows the amino acid sequences of a set of 24 diverse nonapeptide amides

MODES OF CARRYING OUT THE INVENTION

A. Definitions

Figure 1:
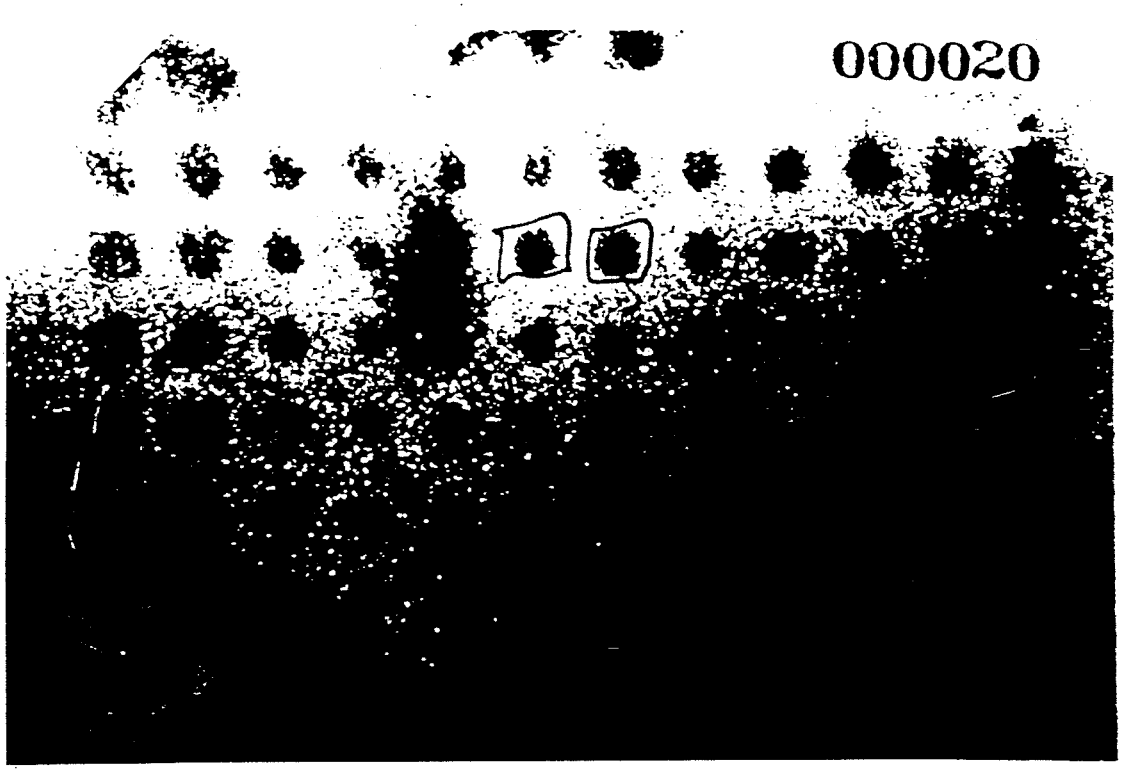
FIG. 1 shows a panel of antibodies bound to solid support according to the method of the invention.

As used herein, "mimotope" refers to the portion of a molecule which has complementarity to the antigen-binding region of an antibody which binds immunospecifically to a desired antigen or analyte—i.e., in general, that region which corresponds to the epitope on the analyte. The mimotope will, in general, not have precisely the same spatial and charge contours as those exhibited by the epitope, but the definition is met if the mimotope, too, causes the molecule in which it resides to bind specifically to the desired antigen-binding antibody. Mimotopes are conveniently short peptide sequences because peptides are easy to synthesize in large variety, but this is not required on theoretical grounds. For example, carbohydrates or detergents might also behave so as to fit this definition; it is simply that the means for obtaining neither a random nor a diverse panel of such mimotopes are encompassed by the currently available synthetic techniques related to these molecules. Individual mimotopes of these chemical types, could, of course, be constructed.

Typically, the epitope reactive with an antibody, for which the mimotope is the substitute, resides in the context of a larger molecule which may, in the case of peptides for example, be an extension of the peptide chain or, similarly, the peptide may be conjugated to some other material. In some cases, the additional parts of the molecule serve particular functions. If the mimotope is to be used as an immunogen, additional size is required, as most mimotope regions are represented by relatively short amino acid sequence regions of 3-6 amino acids. On the other hand, the mimotope may be conjugated to a material which permits labeling. The labeling may be direct, as in the case of a conjugation of a fluorophore or sequestering of a radiolabeled material, or may permit subsequent attachment of labeled material by specific binding, as in the case, for example, of conjugation to biotin for biotin/avidin binding where the avidin would then carry the label. In any event, the mimotope itself is often found in the context of additional molecular structure, and while the term mimotope is defined as relating to the region accounting for antibody binding, the term is often used interchangeably to denote the conjugate. It will be clear from the context whether the entire conjugate or the binding specific region is referred to in a particular instance.

"Antibody fragments" refers to fragments of antibodies which retain the specific binding characteristics of the whole antibody. Particular fragments are well-known in the art, for example, $F(ab')_2$, Fab, and Fab', which are obtained by digestion with various proteases. Of course, if made recombinantly, arbitrary fragments which retain the antigen-recognition characteristics can be obtained, as well. These fragments are often useful in vivo as they are less immunogenic than whole antibodies; there appear to be certain advantages, in in vitro assays, in using fragments in place of antibodies for specific binding as well. Unless specifically otherwise noted, where antibodies are referred to in the context of an in vivo or in vitro assay, it should be understood that immunospecific fragments could also be used.

"Randomly stimulated antibody-producing cells" refers to immortalized antibody-secreting cells which have been stimulated in a nonspecific manner, for example by addition of bacterial lipopolysaccharide (LPS) to the culture. The sampling of the general B-cell population of an individual mammal thus obtained is known to include cells producing antibodies which are specifically reactive with any possible antigen, though at moderate affinity.

"Mimotopes of random contours" refers to mimotopes which contain surface regions of a variety of spatial and charge configurations. As described below, such a random mixture can be achieved by generating peptides of amino acid sequence wherein the amino acid at each individual position is randomly chosen from a substantial number of candidates. However, any mixture of molecules which have a wide variety of surface regions corresponding to potential epitopes is included.

"Mimotopes of maximally diverse properties" refers to a set of mimotopes where various characteristics are deliberately manipulated so as to generate a panel with maximally diverse representative properties. Suitable properties to be considered in constructing diverse panels include, but are not limited to: isoelectric point (pI), hydrophobic index (hi), hydrophobic moment (hm), dipole moment (dm), and "smoothness". By diversifying these properties among members of a panel of mimotopes, the number of mimotopes in the panel can be dramatically reduced, in comparison to panels where comparable diversity is attained by random selection of peptides.

Mixtures of peptides which are "maximally diverse" with respect to a given set of parameter refers to mixtures wherein the members span the entire range of each parameter and the members of the mixture are equally spaced within the range. Appropriate normalization of scales for the various parameters facilitates the diversification process. For example, a mixture of peptides wherein the members are maximally diverse with respect to hydrophobic index indicates a mixture in which representatives are found of the entire range of hydrophobic indices, and no two members of the mixture are substantially closer in value of hydrophobicity index to each other than any other chosen pair. It is understood that perfection with regard to maximal diversity is difficult to achieve, and the term is applied to mixtures where the greatest diversity for the specified parameter is obtainable. Thus, in a mixture which is maximally diverse with respect to hydrophobic index (hi) and with respect to pI, all peptides with similar pI will vary with respect to hydrophobic index, and all peptides with similar hi will vary with respect to pI.

"Inverse or reverse image panels or mixtures" refers to complementarity of the charge/space contours of the epitope/paratope interaction of antigen/antibody interactions. Thus, a panel of monoclonal antibodies in which each member has a high specificity for a single member of a mimotope panel, as compared to the other members of the mimotope panel, constitutes a panel with an inverse or reverse image of the corresponding mimotope panel. Such inverse imaging assumes that for each mimotope in, for example, a 50 member panel, an antibody can be found which has a high affinity for the specified mimotope, and almost no binding to any of the remaining 49. Such panels are most conveniently prepared against a set of maximally diverse mimotopes.

As set forth above, inverse image panels can be used, for example, in competition assays to characterize either analyte or antibodies. Preferably, the members of the inverse image panels are sufficiently small in number so as to constitute a practical set, but a large enough number to give a meaningful pattern. such panels should therefore typically include 10-100 members, preferably about 40-50 members. The reactivity of an analyte with the monoclonal antibody inverse image panel or an antibody with the mimotope panel can be assessed using a variety of techniques as described below.

B. General Description

The invention is directed to procedures for obtaining desired analytical materials for use in immunoassays and to the materials so derived. Some aspects of the procedures involve the use of large numbers of randomly generated antibody-producing cells, and large numbers of potential mimotopes.

As the process of the invention proceeds, the number of antibodies and mimotopes in a particular panel or subset is significantly reduced, and the resulting materials for use in analysis may comprise highly specific and strongly binding mimotopes and antibodies, or, in addition, can be panels of these materials which exhibit characteristic reaction patterns with regard to the analyte. The panels of antibodies obtained become more and more characteristic and specific for the analytical procedures for which they are intended.

In a brief overview, this process begins by generation of a panel of immortalized monoclonal antibody-producing cells which will serve as the starting point for production of materials vis-a-vis any particular chosen analyte. For repetitive screening, it is preferable that this panel be limited to a manageable number, say 10,000 or so; because the number of potential analytes is in the millions, the initial panel will have adequate scope only if specificity is sacrificed. Empirically, even panels much smaller in number, e.g., 300-500, do not sacrifice too much specificity for an initial profile. Broad specificity is an inherent property of randomly stimulated B-cells. These clones produce mostly IgM immunoglobulins. A recombinantly produced set of immunoglobulins can also be used.

If it were practical to produce and screen the millions and millions of possible paratopes required to obtain a precise fit for the repertoire of desired analytes, this could be done directly. However, this is not practical, and therefore the system of the invention provides a way to focus the screening procedure to a practical range of choices.

When the invention is practiced in its simplest form, the basal panel antibody which comes closest to the specificity needed is used to select a mimotope from a randomly generated set, which, again, because it must contain a reasonable number of members, cannot provide each of the millions of available analyte contours with complete fidelity. Therefore, a panel of candidate mimotopes with large scope is used, and the best option selected. Once past this "bootstrap" step, the method of the invention involves systematically optimizing first one, then the other, partner in the antibody/mimotope binding reaction. The criterion for optimization is functionally defined by ability to detect analyte.

Once the initial mimotope is selected, it can substitute for the analyte in stimulating the somatic diversification process of the immune system of an animal, ordinarily activated in response to an antigen. The panel of monoclonal antibodies produced in response to this immunization can then be screened using the analyte in competition with the mimotope, or mixture of mimotopes or using the analyte directly, to select the best candidate. The antibodies, which will be mostly IgG forms, are known to be more diverse than their basal repertoire precursors. In well-studied cases, some exhibit higher, and some lower, affinity for the immunogen. To the degree that the mimotope is an effective substitute antigen, the diversified clones will also include members with higher affinity for the analyte itself. Alternatively, the antibody clones can be randomized in vitro by site directed mutagenesis of the immunoglobulin-coding DNA.

If this improvement is insufficient, the improved antibody could be used for screening a mimotope panel, resulting in, perhaps, the selection of a different mimotope from that previously used; one which more closely matches the analyte. This second selected mimotope can be used for a second immunization to obtain a second panel of in vivo-generated B-cells secreting monoclonals to be screened. This process can be repeated, as well.

In a more elegant and efficient form of this process, the single chosen mimotope or antibody at each step is replaced by a subset having common characteristics of functional homology to the analyte. This is preferable because the particular analyte may have a number of epitopes overlapping to regenerate its entire surface contours, and a collection may together more usefully mimic the entire surface than an individual portion thereof. Conversely, a mimotope may have an extended surface only part of which is homologous to analyte. By using multiple mimotopes and/or antibodies, common features are accentuated. In addition, because antibody subsets provide characteristic and reproducible patterns of interaction with a single analyte which are different from those generated with related analytes, specificity can be imparted by the pattern itself rather than by the reactivity of an individual antibody, per se.

Thus, in this modified procedure, a small number, say 10 or 15, of the original antibody panel, is used to screen the panel of mimotopes. The mimotope panel results yield still another subset, say 10 or 15, of mimotopes which can be used for immunization. The immune system of the immunized animal is thus most intensely exposed to the common features, and the panel of monoclonals obtained from the immunized animal may then well be skewed in the direction of these common features. (Chua, M. M., *J Immunol* (1987) 138:1281-1288.) In addition, the panel obtained from the immunized animal, either in this case or where only a single mimotope is used, provides subset panels useful by their binding array in the recognition of particular analytes by virtue of the pattern of binding specificities across the panel.

The following, in more detail, describes each of the steps involved in the method of the invention.

C. Production of Starting Materials

The Initial Antibody Panel

The random panel of antibody-producing cells can be generated in several ways. It has been known for almost 10 years that mitogen activated B-cells produce a random set of antibodies which potentially are capable of binding any possible antigen. However, most of the immunoglobulins secreted by these stimulated cells are IgMs, and are of relatively low affinity and specificity. The manageable repertoire appears sufficient to bind at some level to any of the many millions of antigens against which defense might be needed; therefore, cross-reactivity is required.

Immortalization of large numbers of B-cells which have been previously stimulated using mitogens such as lipopolysaccharide (LPS) by cell fusion or viral infection results in a generally permanent source of large numbers of a wide variety of antibodies. LPS stimulation causes partial differentiation of the B-cells, thus making them good fusion participants. Methods for stimulating the production of antibodies and for performing such fusions have been disclosed, for example, by Andersson, J., et al, *Current Topics on Microbiol and Immunol* (1978) 81:130-138; Andersson, J., et al, *Proc Natl Acad Sci USA* (1981) 78:2497-2501; Goldsby, R. A., et al, *Current Microbiol* (1979) 2:157162. Additional methods for preserving the lymphocytes other than fusion are reported by Howard, M., et al, *Proc Natl Acad Sci USA* (1981) 78:5788-5792, and sorting of these hybridomas for antigen specificity was reported by Parks, D. R., et al, *Proc Natl Acad Sci USA* (1979) 1962-1966. Production of hybridomas which secrete immunoglobulins specific to antigens which have been used as immunogens in vitro has also been described (Luben, R. A., et al, *Molecular Immunol* (1980) 17:635-639).

In order to make the numbers more manageable, a modification of the general use of a large random panel involves presorting to narrow the panel to the best candidates. For example, Casali, P., et al, *Science* (1986) 234:476-479 describe the use of a fluorescence activated cell sorter to segregate human lymphocytes capable of binding to a labeled antigen. The individual cells could then be recovered, and transformed with Epstein-Barr virus to be grown in microculture. Such preselection is possible within the context of the present invention if the desired analyte can effectively be labeled. If such labeling can be effected, for example by direct conjugation of the analyte to fluorescein, or by conjugation to a linker moiety such as avidin for association with fluorescence-labeled biotin, the procedure described by Casali (incorporated herein by reference) can be used to obtain a limited, for example, 10-50 member panel of monoclonals for subsequent screening of the mimotope panel. Immortalization of the selected cells need not necessarily be by use of Epstein-Barr virus, but may be by standard fusion techniques or by the efficient electrofusion techniques now available, such as those commercially available from Biotechnologies and Experimental Research Incorporated (San Diego, Calif.).

More recently, it has been possible to produce immunoglobulins using recombinant techniques. Therefore, an alternate procedure for obtaining a random panel of antibody producing cells comprises randomly mutagenizing immunoglobulin-encoding DNA and transfecting the mutated mixture into cells capable of expression of the encoded mutated immunoglobulins. Immunoglobulin proteins have been expressed successfully in *E. coli* and in yeast and yeast processes the proteins produced into immunologically active forms. For example, synthesis of immunoglobulins and their in vivo assembly in yeast has been reported by Wood, C. R., et al, *Nature* (1980) 314:446-448. Synthesis in *E. coli* of both "native" and "dimeric" antibody fragments capable of binding antigen has also been reported (Skerra, A. *Science* (1988) 240:1038-1041; Butler, M., et al, ibid:10-41-1043).

By any of the foregoing methods, a panel of cells, either immortalized B-cells, or recombinant host cells containing expression systems for immunoglobulins may be obtained. If a totally random panel is used a panel of about 10,000 members may be needed. A panel of at least 50,000 members provides a better cross-section. However, recent empirical work indicates that smaller numbers may be satisfactory for some purposes.

The results of such work are shown in FIG. 2. FIG. 2A shows the binding constants for 335 monoclonal antibodies generated as described in Example 1 herein and screened quantitatively against the short peptide kassinin to determine "binding coefficient", i.e., the binding observed corrected for background. (Screening was done by a variant of the commercially available Bio-Rad dot blot method. As shown in FIG. 2A, only one of the 335 Mabs has a binding coefficient of 3500-4000; two additional Mabs have binding coefficients of 1500 or so, and there are a few antibodies with binding coefficients of about a thousand, but the majority are very low binding to this very simple antigen.

Figure 2A:
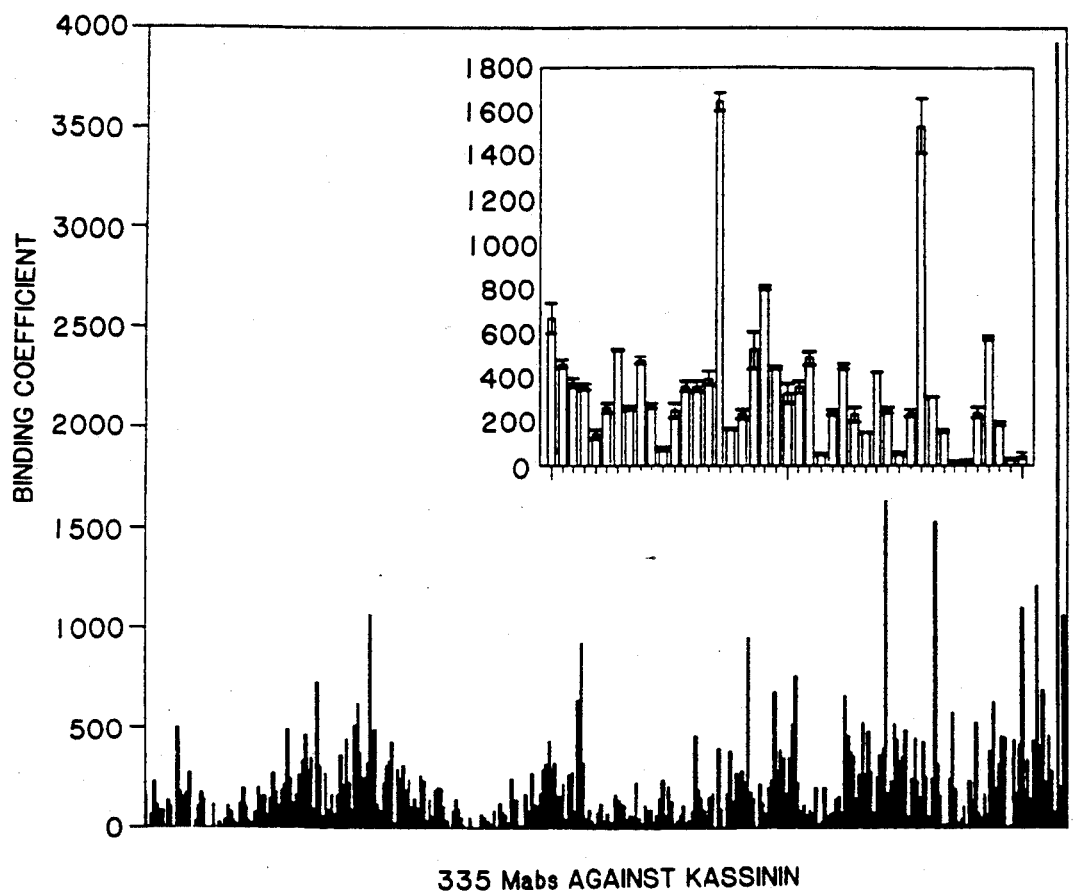
FIGS. 2A, 2B and 2C show the patterns of binding coefficients for a 335 member basal antibody panel with respect to three different antigens, kassinin, phage F1, and KLH, respectively.
Figure 2B:
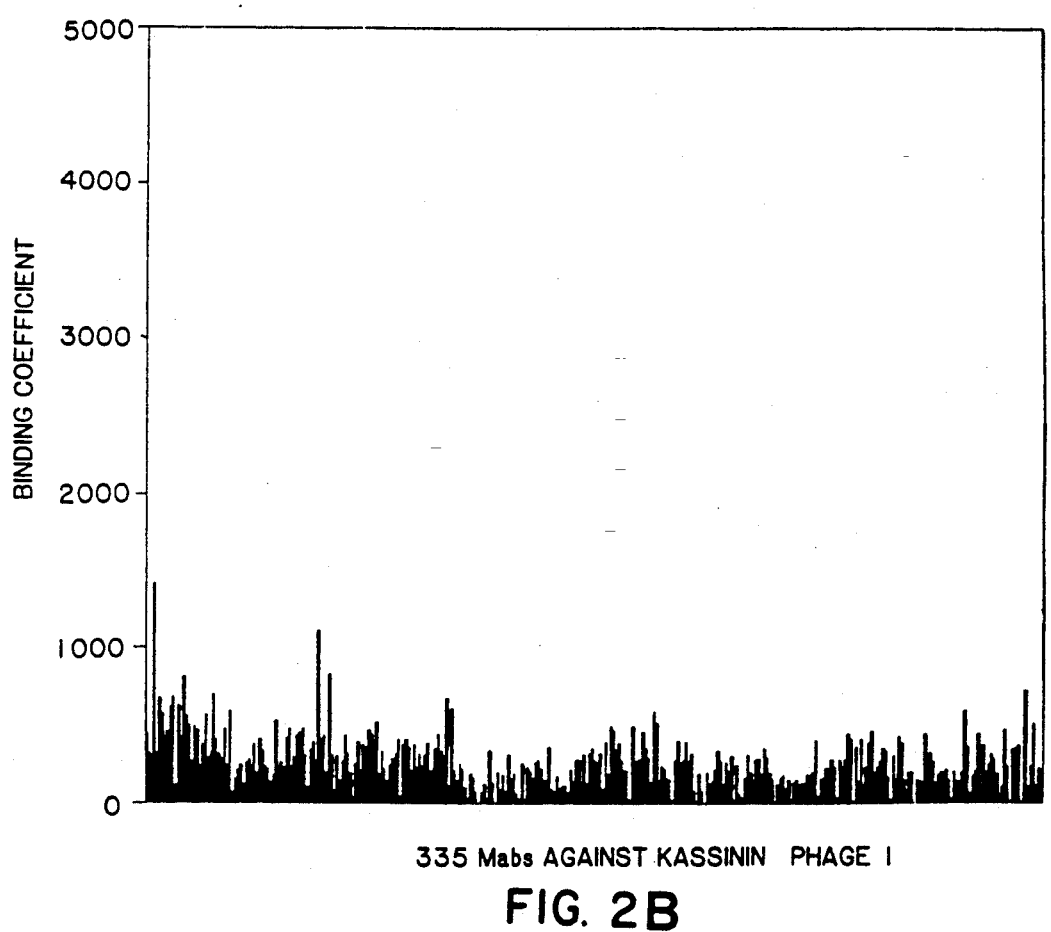

FIG. 2B shows the same results tested against a more complex antigen, the simple filamentous phage F1. In this instance, with a few epitopes repeated randomly a large number of times, almost all of the panel has substantial binding for the antigen where presumably binding is increased by the multivalent nature of IgM.

Figure 2C:
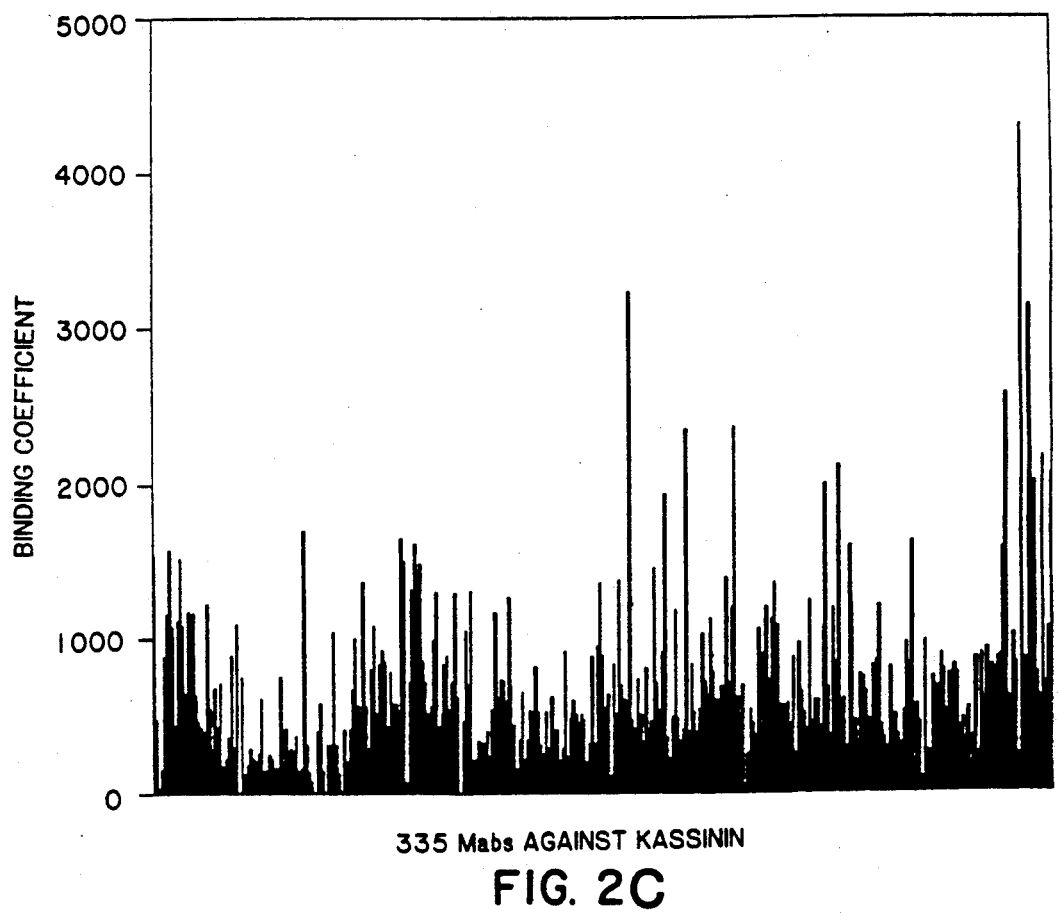

FIG. 2C shows the results when similar assays were performed against a highly complex antigen, keyhole limpet hemocyanin (KLH). In this case, there are more epitopes present and consequently, there are larger numbers of antibodies with substantial affinity for the antigen.

Figure 2D:
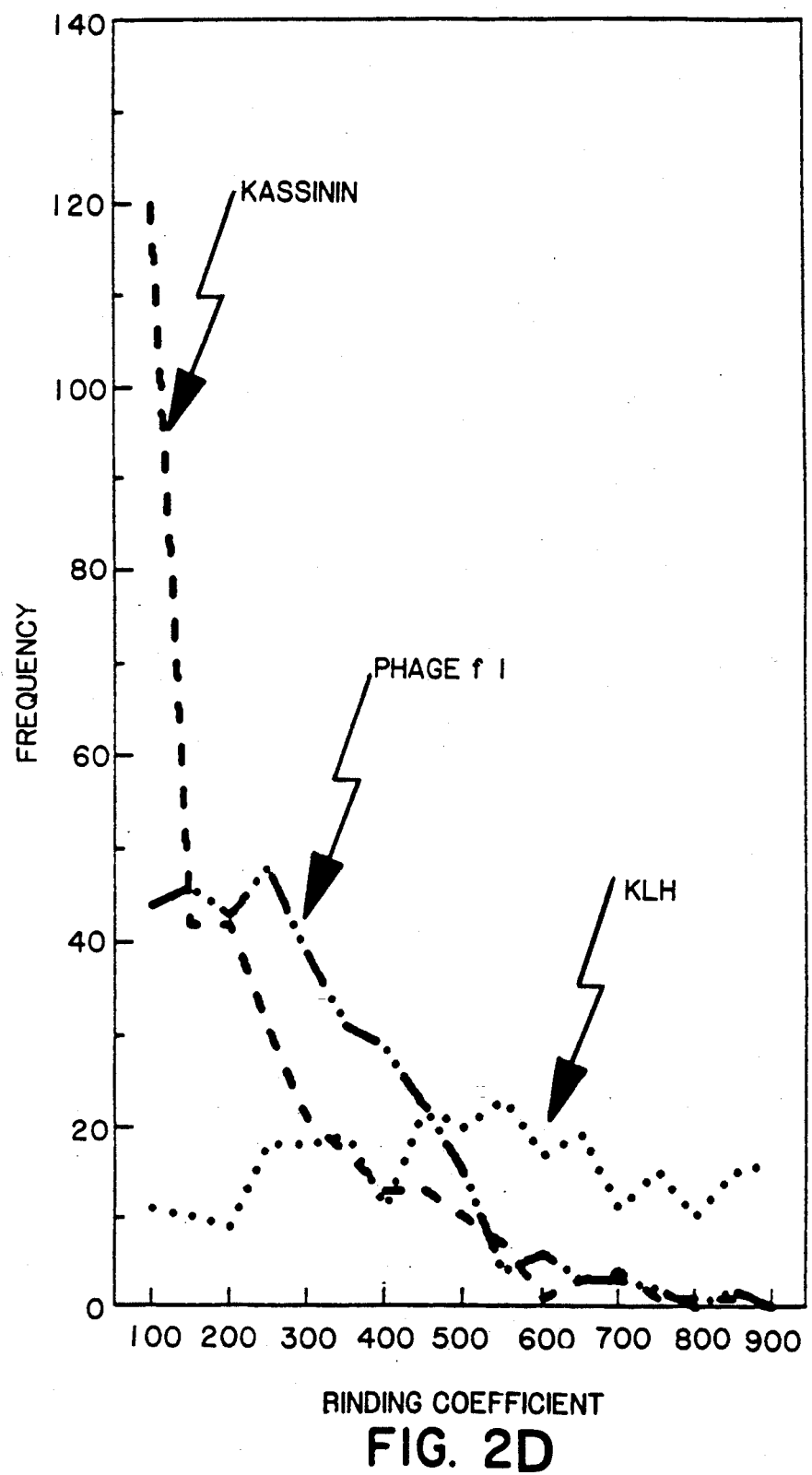
FIG. 2D is a graphical representation of the results shown in FIGS. 2A-2C.

The results shown in FIGS. 2A, 2B and 2C are summarized in FIG. 2D which plots the distribution of binding coefficients in the murine basal repertoire for these three materials. As shown in the figure, the percentage of monoclonals with high binding for kassinin is quite low; nevertheless, within the panel of only 335

Mabs, at least a few antibodies of substantial affinity are found.

These results have several important consequences. First, the basal panel need not be overly large if the antigen is of the correct complexity to assure segregation among small numbers of antibodies in the panel, as is the situation in FIG. 2A. Second, the subset panel of high binding Mabs itself can be a useful analytical tool. The "fingerprint" of kassinin vis-a-vis this panel, derived from the pattern shown in FIG. 2A, can be used effectively to monitor kassinin levels in test samples. Increases or decreases in the levels of kassinin can be demonstrated by internally consistent determinations of binding to two or three high binding antibodies.

However the basal monoclonal antibody panel is prepared, these cultures can be grown in microtiter plates or on other convenient substrates which permit easy analysis of the supernatants with regard to ability to bind analyte or mimotopes. One aspect of the invention is directed to a kit, which kit comprises this or a later produced panel of antibody-producing cells supported on an appropriate substrate for screening in the procedures of the invention. Suitable configurations of the kit include microtiter plates, nitrocellulose, activated forms of nylon or other polymers available as sheets, and derivatized agarose solidified into filter paper.

As the initial random panel is believed to represent a collection of antibodies which sacrifices specificity and affinity for scope, where large numbers of members are required, it is less useful for inclusion in a kit for analysis of a particular analyte than as a means to produce additional materials useful in analysis of a wide range of analytes. Accordingly, this panel is more appropriately kept as a production and research tool than packaged as a test kit. However, a subset of these initially produced antibodies may produce a characteristic enough pattern with regard to a particular analyte that it can serve as a test substrate, as well.

The Mimotopes

Also needed in the initial phases of the invention procedure is a mixture of mimotopes, some of which are capable of mimicking, at least to a satisfactory degree, the binding ability of the analyte. An early attempt to provide synthetic epitopes for an antigen of known 3-dimensional structure is described, for example, by Atassi, M. Z., et al, *J Biochem* (1977) 252:8784–8787.

As mentioned above, the chemical nature of the mimotopes is a matter of convenience rather than of theoretical significance. Two extremes in approaches to constructing a set of potential mimotopes can be employed. In one approach, a random set involves very large numbers of members. A convenient source of a random and wide variety of three-dimensional molecular architecture is the synthesis of 3-6 amino acid peptides of random sequence. Utilizing only the 20 formally encoded amino acids, there are $20^3$ or 8,000 possible tripeptides. A mixture of at least 500 tripeptides is needed, 5,000 or 10,000 is preferred. The number actually needed may be minimized by optimizing the choice of residues. For example, substitution of alanine for valine will not represent a materially different peptide, whereas substitution of alanine for tyrosine will matter greatly. Of course the number of theoretically possible mimotopes for a 3-amino acid sequence can be at least multiplied by eight by doubling the number of amino acid candidates, if synthetic peptide methods are used.

This can be done by including an additional 20 amino acids with modified side chains as candidates for inclusion in the sequence or by including the D-isomers. In this case, one would obtain $40^3$ possible tripeptides. One approach to providing large numbers of mimotope structures is described by Geysen, H. M., W06/00991 (supra), where multiple peptides are simultaneously obtained by introducing multiple residues in the chain elongation step on multiple supports for solid phase synthesis. Geysen has also described testing an antibody against all 400 possible "natural" dipeptides as a starting point for mimotope construction. The number of available peptides when the peptide chain is increased over the region of epitope size (up to six amino acids), of course, increases accordingly.

An even more randomly constructed, but not necessarily more diverse, panel of multiple mimotopes can be obtained by drastic hydrolysis of protein mixtures found in nature. For example, yeast extract can be hydrolyzed with a mixture or sequential treatment with proteases such as trypsin, chymotrypsin, collagenase, chymosin, enterokinase, and so forth. The resultant is a large number of small molecular weight proteins which can be separated, if desired, on SDS gels and labeled using, for example, the Bolton-Hunter $^{125}$I method. These individual SDS bands have been shown to be capable of transfer to Western blot paper to obtain a panel of individual mimotopes. The unlabeled transferred mimotopes or mimotopes labeled in a manner compatible with subsequent labeling when the mimotopes are bound to candidate antibodies can be used as a means to identify candidate mimotopes vis-a-vis preselected members of the basal repertoire.

A different and preferred approach to constructing a set of mimotopes is the construction of a maximally diverse set. This set achieves the above-referenced minimization of numbers by optimizing the choice of residues to a refined level. Conceptually, the construction of a diverse set of mimotopes, such as peptides, is formulated by designing peptides in which certain defined properties are systematically varied over the full range. Suitable properties for consideration are overall charge on the peptide, overall hydrophobicity, its hydrophobic moment, the general character of its contours (i.e., smooth or rough) and the distribution of charge. If peptides are used, as would be the most convenient embodiment for the mimotopes, these characteristics can be predicted from the amino acid sequences using the known characteristics of the amino acids employed and data derived from X-ray crystallographic analysis of proteins.

In addition, as the 3-dimensional conformation of peptides fluctuates due to thermal agitation, it may be useful to employ means to stabilize the desired conformations. Means are known in the art to restrict conformation of peptides (see, for example, Weber, D. F., et al, *Nature* (1981) 292:55–58; Friedinger, R. M., et al, *Science* (1980) 210:656–658).

By way of illustration, one embodiment of this approach to a panel of 6-mers is as follows: The parameters which determine electron cloud patterns should be varied widely over the candidates. For example, the prepared candidate peptides should be chosen so that the hydrophobicity index steadily increases across the panel. A discussion of hydrophobicity indices as related to structure is found in Janin, J., *Nature* (1979) 277:491–492. In addition, the amphipathic qualities of the proteins can be varied by adjusting the periodic hydrophobicity of the residues (Eisenberg, D., et al, *Proc Natl Acad Sci USA* (1984) 81:140-144; Eisenberg, D., et al, *Nature* (1982) 299:371-374). The amphipathic property resides in the secondary or tertiary conformation of the peptide, resulting in portions or faces of the molecule which are water soluble and others which are hydrophobic. In addition, the charge pattern due to the presence of positively or negatively charged amino acid residues can also be varied systematically in the candidate panel.

An initial candidate panel, diverse in these parameters, can conveniently consist of about 90-100 peptides for convenience, as a reflection of the design of commercially available microtitre plates and protein synthesizer rods (Cambridge Research Biochemicals). This is a sufficient number to frame the characteristics of the desired mimotope. The synthesis is conducted using conventional, usually commercially available, methods, and the panel of individual candidate mimotopes is then ready for screening.

A more complete diversification can be formulated using additional properties of the amino acids. In construction of this more diverse panel, the individual amino acid properties known from the literature are employed. Table 1 below is a compilation of these properties for 19 of the 20 encoded amino acids. Cysteine is not included in the table or in the set, as it is convenient to use this residue for conjugation to additional moieties such as label, carrier, solid supports, etc.

TABLE 1

|     |   | hydrophobic index | pka | chg pH 7 | volume ($A^3$) | Rel freq |
|-----|---|-------------------|-------|----------|----------------|----------|
| Ala | A | 0.25              | X     | 0        | 91.5           | 6        |
| Asp | D | −0.72             | 3.86  | −1       | 124.5          | 6        |
| Glu | E | −0.62             | 4.25  | −1       | 155.1          | 6        |
| Phe | F | 0.61              | X     | 0        | 203.4          | 4        |
| Gly | G | 0.16              | X     | 0        | 66.4           | 7        |
| His | H | −0.40             | 6.0   | +0.1     | 167.3          | 3        |
| Ile | I | 0.73              | X     | 0        | 168.8          | 4        |
| Lys | K | −1.10             | 10.53 | +1       | 171.3          | 7        |
| Leu | L | 0.53              | X     | 0        | 167.9          | 7        |
| Met | M | 0.26              | X     | 0        | 170.8          | 2        |
| Asn | N | −0.64             | X     | 0        | 135.2          | 4        |
| Pro | P | −0.07             | X     | 0        | 129.3          | 5        |
| Gln | Q | −0.69             | X     | 0        | 161.1          | 4        |
| Arg | R | −1.76             | 12.48 | +1       | 210.9          | 4        |
| Ser | S | −0.26             | X     | 0        | 99.1           | 8        |
| Thr | T | −0.18             | X     | 0        | 122.1          | 6        |
| Val | V | 0.54              | X     | 0        | 141.7          | 6        |
| Trp | W | 0.37              | X     | 0        | 237.6          | 2        |
| Tyr | Y | 0.02              | 10.07 | 0        | 203.6          | 3        |

From the parameters in Table 1, 5 parameters can be obtained which can then be varied over the set. These parameters are as follows:

1) Hydrophobic index (hi) is the sum over the amino acids in the peptide of the individual hydrophobic indices of the amino acid components. This can be formulated for a peptide of n amino acids by the formula:

$$hi \text{ (peptide)} = \sum_{i=1}^{n} (hi)_i.$$

2) Isoelectric point (or pI) can be approximated as the average of the $pK_a$s of the ionizable groups.

The third, fourth and fifth parameters are conformation dependent, and can be labeled as the hydrophobic moment (hm), the dipole moment (dm), and the "corrugation factor" (cf), which measures smoothness. These parameters are calculated by similar approaches which are, in each case, the modulus of the Fourier transform of the appropriate property function—i.e., the strength of the component of periodicity of period-δ, where δ is defined to match an α-helix (100°), or a β sheet (170°). The assignment of the proper δ value will depend on the conformation normally assumed by the peptide, or that into which it is controlled by the designer of the peptide.

It is recognized, however, that the general relationships of the resulting parameters among members of a set do not appreciably change regardless of the assumptions made about the conformation. Thus, if the above parameters are calculated for all members of the set assuming, for example, an α-helix conformation, the pattern of results will not vary appreciably from the "true" pattern, even if the peptides in fact are not in the form of α-helices. This result is particularly important in regard to very short peptides of insufficient length to attain a recognized, ordered conformation.

Therefore, the calculations of the three parameters, hydrophobic moment (hm), dipole moment (dm), and corrugation factor (cf) are as follows:

$$\mu(\delta) = \left\{ \left[ \sum_{n=1}^{N} H_n \sin(\delta n) \right]^2 + \left[ \sum_{n=1}^{N} H_n \cos(\delta n) \right]^2 \right\}^{\frac{1}{2}} =$$

$$\left| \sum_{n=1}^{N} H_n e^{i\delta n} \right|$$

wherein for hm, H=hi, for dm, H=overall charge at pH 7, and for cf, H=volume.

The generation of the diverse set based on maximizing the variation in these 5 parameters, can be accomplished using a variety of sorting techniques, but a particularly preferred approach is described as follows: Candidate peptide sequences are formulated randomly and then sorted for differences from previous chosen candidates with respect to each of the 5 parameters. The candidate peptides are randomly chosen from a pool of a convenient number, say 90-100 sources of 19 individual amino acids distributed in the 90-100 sources according to their frequencies in naturally occurring proteins. As shown in Table 1, some amino acids appear in natural proteins with greater frequency than others, a frequency that is generally measured by the level of redundancy of the codon associated with this amino acid in the genetic code.

The first formulated 6-mer, for example, will have each position filled by an amino acid randomly chosen from the panel of 90-100 sources. The next candidate, also constructed by a random selection from the 90-100 sources, will be compared to the first candidate for differences in the 5 measured and calculated parameters. Depending on whether there are substantial differences, this candidate peptide will be retained or discarded. As more and more candidates are tested, of course, the greater is the likelihood that the candidate will have properties too close to one already in the set to warrant retention, and the larger number of candidates that will need to be formulated and screened before the member is retained in the set. The process will continue until the number of candidates examined since the last one was accepted becomes unacceptable. In general, the pattern expected is as shown in FIG. 9.

Figure 9:
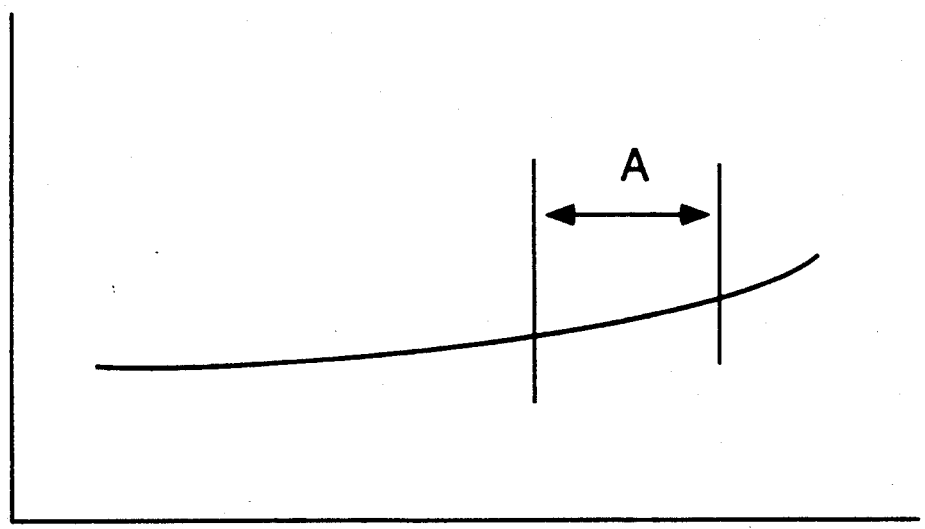
FIG. 9 shows a graph of the pattern expected as a result of testing multiple candidate peptides for optimal diversity.

FIG. 9 plots the number of peptides considered on the X axis and the number of peptides considered since the last accepted peptide on the Y axis. The indicated portion of the curve shown as region "A" describes a region where the process becomes too cumbersome and the formulation and selection process should therefore cease somewhere in the indicated region.

In order to obtain a final panel of 48, it is preferred to provide initially approximately 96 diverse candidates to permit final fine tuning by hand. For example, the dipole moments of the sidechains as compared to the dipole moment of the backbone might be considered. The final panel should be reviewed so that a distribution of properties exists for all parameters—i.e., each peptide differs from all others by at least X% (after normalization of the scale to the range of 0–100 units), the value of X being determined by the "cumbersome" zone on the graph. Thus, each peptide is substantially different from all other peptides in the set with regard to at least one of the five parameters. This approach is advantageous because computation is easier than synthesis. Full diversity is however, to some extent undermined due to thermally induced fluctuations in conformation.

The validity of using representative samples to decrease the total number of members of a panel in a screening assay is recognized in a number of contexts. See, for example, Carey, W. P., et al, *Anal Chem* (1987) 59:1529–1534; Skilling, J., *Nature* (1984) 309:748–749.

When the peptides in the candidate mimotope set have been chosen, the individual peptides are readily obtainable using known technology. For example, the "T-bag" synthesis method of Houghten, R., *Proc Natl Acad Sci USA* (1985) 82:5131–5135, permits the synthesis of macroscopic quantities of these materials. In addition, the synthesis of large numbers of peptides bound to a polyethylene solid support for exploration of antigen structure and used to obtain an understanding of antigen/antibody interreactions has been reported by Geysen, H. M., *Immunol Today* (1985) 6:364–369; Geysen, H. M., et al, *Molecular Immunol* (1986) 23:709–715; Geysen, H. M., Australian patent specification 25429/84.

The synthetic mimotope mixture can also be prepared using randomly synthesized DNA sequences shotgun cloned into λ phage vectors, for example, for expression in phage-transfected hosts. In this approach, standard commercially available solid phase DNA synthesis techniques are used to synthesize 9-mers, 12-mers, 15-mers or 18-mers of random sequence, with further extensions of uniform sequence, if desired, and ligated to standard expression systems for transfection into host cells. Any recombinant host could be used, but a convenient expression system comprises λ phage vectors and bacterial host cells. Such transfected materials can be then cultured under suitable conditions for expression to obtain the mixture of mimotopes, or, if a panel rather than a mixture is desired, as will be discussed below, the transfected *E. coli* can be plated out as individual colonies for generation of individual peptides. Expression systems suitable for peptide sequences are known in the art and may be found, for example, in Maniatis, *Laboratory Cloning Manual* (1982) Cold Spring Harbor Press, and are generally known in the art. Recombinantly obtained peptides also may be obtained as mixtures or as individual peptide sequences.

It should again be emphasized that while polypeptides are extremely convenient to synthesize, the choice of potential mimotopes should not be limited to amino acid sequences. The amino acid sequences themselves may be derived from both naturally occurring amino acids and those which do not occur in nature, and those which may occur in nature, but are not encoded by the genetic code. In addition, polysaccharide complex structures and chemically synthesized variations of polycyclic structures containing a variety of substituents to alter their shapes and electron distribution, could also be used. However, the use of polypeptides permits the access of currently available technology and a rapid realization of a large number of variants which probably provide the spectrum of desired shapes without need to invoke the use of other synthetic approaches to obtain a representative sample of antigen surface contours.

D. Screening Procedures

Immunoglobulins Reactive with Target Analyte

One phase of the invention procedure relates to a method to obtain antibodies reactive with a desired analyte. In some instances this may require only a single iteration employing the randomly generated antibody panel. In this procedure, presumably, the antibody panel could be screened directly with the analyte. However, this has the disadvantage that the analyte must be available in quantity, must be chemically altered in order to provide the label, or must otherwise must be conjugated to some modifying material which can, in turn, bind label. In the method of the invention, this is avoided by competition of the unlabeled analyte with a labeled mixture of mimotopes. Labeling of the mimotope mixture can readily be accomplished by conjugating to the peptide chain a linker molecule, perhaps as simple as a cysteine residue, which then can be conjugated to label using commercially available linkers, such as those sold by Pierce Chemical Co. Alternatively, the peptide can be conjugated to other proteins, such as avidin, which then can be used as means to attach label. The label may be of a variety of choices, including an enzyme, fluorophore, radioactive moiety, chromophore, and the like. Typical enzyme labels include horseradish peroxidase, trypsin, catalase, and alcohol dehydrogenase. Fluorophores include fluorescein and dansyl. Chromophores, such as various dyes, may also be used. The number of possible labels is large and well known to those in the art. The label may be conjugated to the mimotope through a spacer which typically would comprise a peptide homopolymer or other simple peptide, or short oligomers of appropriate solubility, such as polyethylene glycol.

The panel is then, as a control, preliminarily tested for its ability to bind to the mimotope mixture. The pattern of binding and intensity of labeling is observed and, in a preferred procedure, antibodies which bind poorly to mimotopes disregarded. Not a great percentage of the antibody panel will fall into this category as the mixture of mimotopes is of sufficient number to contain a large variety of possible contours, and thus should contain at least a few members capable of binding to any conceivable antibody. This is particularly the case for a mimotope mixture of maximum diversity. The panel in which all members have now been demonstrated to bind the mimotope mixture, is rescreened using unlabeled analyte in competition with the mimotope mixture. Serial dilutions of the analyte and mimotope mixtures (or individual components) are used to ascertain those antibodies for which the analyte most successfully competes.

In more detail, the mixture of the requisite number of mimotopes (roughly on the order of 10-1000, depending on the inherent diversity; for more diverse mixtures, numbers in the low end of the range will suffice) is labeled in a suitable manner, for example using the acyl iodination method with the iodine isotope 125 as described by Bolton, A. E., et al, *Biochem J* (1973) 529-539, and available commercially from ICN Radiochemicals. Other labeling methods, such as avidin/biotin linked fluorescein, can also be used. As noted above, a mixture of peptides can be prepared directly by synthesis of individual members and mixing them together or can be obtained by hydrolysis of large proteins into random small peptides. One approach, for example, utilizes a partial trypsin hydrolysate (Cleveland, D. W., et al, *J Biol Chem* (1977) 252:1102-1106) of a yeast lysate. This provides a large number of peptides which can be labeled as a mixture, or which can be separated using, for example, SDS gel electrophoresis and transferred to a test support such as Immunodyne (Burnette, W. N. *Anal Biochem* (1981) 112:195-203 if their binding is to be assessed individually.

It may be necessary in utilizing the labeled peptide mixture to verify that satisfactory binding occurs with regard to all candidate antibodies in the panel. The conditions for effecting this equivalent binding throughout the panel should also be established empirically. In a perfect situation, the peptide mixture will bind uniformly to all panel members. However, more frequently, only similar levels of binding are found. This provides a perfectly workable basis for competition with analyte, as interpretation of results when competition is added can be simplified by normalization of the binding values of the members of the panel to the mixture to the same value, i.e., 100%, before evaluating the competition.

When it is confirmed that the labeled peptide mixture binds roughly equivalently to all candidate antibodies in the absence of analyte, or similar binding has been normalized, the screen is repeated in the presence of analyte. Those candidates which have specific affinity for analyte will show a decrease in the binding of labeled peptide mixture, the decrease being proportional to the specific affinity of the candidate for the analyte. The antibodies with greatest affinity to the analyte show the lowest levels of labeling as this indicates successful competition of the analyte with the labeled mimotope mixture for the antibody. By assessing the ability of the analyte to compete, those antibodies which show the greatest decrease in label uptake are selected as having the parameters that are most favorable for binding analyte.

It is sometimes the case that an antibody-producing cell or a subset of the panel discerned in this way has sufficient specificity and affinity for the desired analyte to be useful in immunoassays without further procedures. If this is the case, the immortalized cell line or cell lines provide a permanent source for the desired antibody or subset, and immunoassays for the analyte can be performed using this antibody or subset as the specific reagent.

A variety of protocols for such assays is available, as is well understood in the art. For example, the sample to be tested might be coated onto microtiter plates, the plates then treated with the identified antibody and then washed. Labeled antibodies reactive with the species characteristics (e.g., anti-murine or anti-goat) of this antigen-specific antibody can then be used to detect the presence of bound antibody. This protocol is, of course, only one of many that might be employed, and variations are well known in the art.

In other protocols, for example, the analyte could be measured using a competition assay which would normally employ a labeled analyte to compete with the unlabeled analyte in the sample. This has the disadvantage, again, of requiring large amounts of analyte and chemical modification thereof; the necessity for additional analyte can, however, be avoided by using the appropriate mimotope (as determined below) as the competitor.

For a subset chosen in this fashion, or a subset chosen at random, in some instance, the specificity may be provided by the pattern of intensity of binding of the analyte with regard to the individual members of the panel. As indicated by the results set forth in FIG. 2, for simple analytes, a characteristic pattern may be obtained in a relatively small random subset. In order to employ this concept, the subset is supported in a convenient pattern on a substrate, and the intensity of binding of the analyte with respect to each antibody measured, so that a pattern emerges. If properly designed, this might be directly read, for example, from a card containing a matrix of, say, 10-10,000, preferably 10-100, such antibodies. Thus, in a preferred approach, one or multiple supports having patterned arrays of the subset are obtained, either by blotting or otherwise transferring supernatants from the individual cell lines.

The pattern panel is standardized for analyte, typically by a suitable protocol which establishes the intensity of binding of the analyte to each member of the panel. One approach to this calibration is treatment of the panel with purified analyte and use of a quantitative detection system such as the antispecies-labeled antibodies described above. Alternatively, an inverse standardization pattern can be obtained by competing unlabeled analyte with the labeled mimotope mixture. The calibrated panel can then be used to analyze sample for analyte by the direct or competitive protocol described and monitoring of a consistent pattern of quantitative binding consistent with that on the calibration panel. Where the fluctuations in the amounts of label obtained are either measured directly as described or competitively between the sample and labeled analyte, labeled mimotope mimicking the analyte as identified in a manner described below, or labeled mixture, these indicate fluctuations in the amount of analyte. In any case, the pattern obtained would be characteristic for the individual analyte, and the same panel or group of panels provides an appropriate test system by pattern recognition.

The recognized pattern can be made quantitative, as well, for use in monitoring the level of analyte in a series of samples, for example, in monitoring chemical processing, waste processing, or other ongoing procedures. Where the analyte is present at variable levels, the intensity of binding in the recognized pattern will be a function of analyte concentration in the series. Several analytes can be simultaneously measured to the extent that their recognition patterns do not overlap on the same panel, and signals from irrelevant, uncharacterized contaminants do not interfere if their fluctuations are small relative to those of the analyte.

Figure 5:
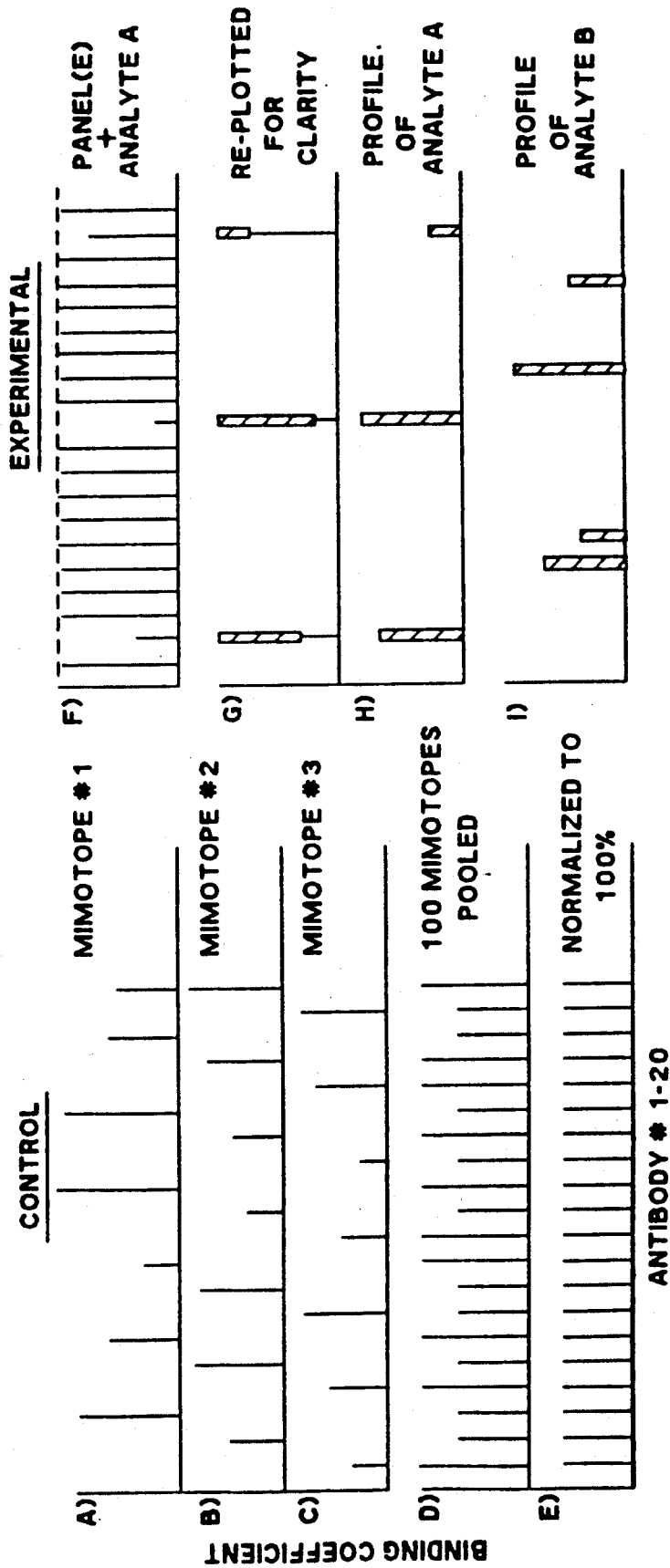
FIG. 5 shows the development of an analyte profile.

An illustration of the use of diverse antibody panels to provide a characteristic profile for a particular analyte is shown in FIG. 5. An antibody panel is constructed using a diverse set of antibodies selected, for example, from one or several of the random panels such that each antibody in the panel has a different qualitative or quantitative reactivity with one or more particular analytes. In FIG. 5, the antibody panel consists of 20 antibodies; however, a greater or fewer number of antibodies may be used.

To verify differential activity with the several mimotopes in a mixture of, say, N mimotopes, each antibody of the panel is reacted with each of the N mimotopes, suitably labeled, such as by radioactivity, to give a detectable signal. Each such mimotope (Mtp) reacted with the panel of antibodies generates a binding profile for the panel which is characteristic of the particular mimotope Mtp-1, Mtp-2, . . . Mtp-N (FIG. 5, panels A-C). The binding signals for each of mimotopes 1-N are then added for each antibody of the panel to generate a characteristic summation profile (panel D) for the set of N mimotopes with respect to each antibody of the panel. Panel D thus also represents a mixture of the N mimotopes. The summations of the mimotope binding signals for each of the antibodies are then "normalized" such that the summation signal represents the maximum (100%) binding for each antibody (panel E).

The profile or fingerprint characteristic for a given analyte or antigen of interest ("Ag A") is obtained by competitively reacting Ag A and a labeled mixture of mimotopes 1-N with each antibody in the panel. The competition profile generated by Ag A (panel F) will generally result in a reduction in binding of the labeled mimotopes with some of the antibodies in the panel due to successful competition of Ag A for certain antibodies of the panel. Panel F of FIG. 5 shows that Ag A caused reduced binding of the labeled mixture of N mimotopes with four antibodies of the panel.

The amount (or reduction) in binding exhibited by those antibodies for which Ag A successfully competed with the labeled mimotope mixture is determined (panel G), and the amount (or reduction) in binding for each antibody in the panel is replotted to generate an antibody binding profile (panel H) which is characteristic of Ag A when compared with other profiles for other analytes (Ag B, panel I) using the same reference panel of antibodies, and the same mimotope mixture competitive set.

It is readily seen that choice of a diverse set of antibodies for use in the antibody panel can result in an individualized profile for an analyte that can be valuable for detection and quantitation thereof.

Selection of a Mimotope Competitive with Analyte

In order to select the appropriate competitive mimotope(s), the mimotope mixture must itself be segregated into a panel and screened. The screening tool (probe) is already available in the form of the antibody-(ies) selected from the original panel. In this phase, the mimotopes are provided as individual compounds, typically on a solid support, such as nitrocellulose, microtiter plates, or the multi-pegged system of Geysen. If the panel is provided on a solid support, it is most convenient to use unlabeled (or ineffectively labeled) mimotope and to provide the label conjugated to the selected screening antibody or to a secondary detecting antibody. The individual mimotopes are then screened directly or indirectly with labeled antibody. An individual antibody may be used, or a subset containing several. A subset may be advantageous, in view of the general lack of specificity of the individual members of the initial panel. Those which bind most successfully are selected for the screening subset. In the alternative, the mimotope mixture can be screened using successively smaller subsets of the mimotope mixture until a suitable binding mimotope is obtained.

It is advantageous to screen the mimotope panel both directly with labeled antibody and in a competition assay. The subset of mimotopes which satisfactorily bind antibody are again screened with respect to the ability of the analyte to disrupt this binding. Those with which the analyte most successfully competes evidently mimic the analyte most completely, and these are the suitable candidates for further refinement of antibody specificity using immunization. This is also the appropriate choice for use directly in immunoassays, as described in the following paragraph.

Selection of the appropriate subgroup or individual mimotope thus provides the needed reagent for competitive immunoassays, wherein the labeled mimotope serves as the competitor to the analyte.

Suitable kits for performing an assay for analyte also form part of the invention. The contents of the kit will depend on the design of the assay protocol for detection or measurement. All kits will contain instructions for performing the assay, appropriate reagents and label, and solid supports, as needed. If the kit is designed for a simple detection assay for analyte using a single highly specific antibody, the kit will contain this highly specific antibody and some means of detecting the reaction of this antibody with analyte. For example, the detection reagent may simply comprise labeling the specific antibody itself, where the assay is conducted by nonspecifically binding the analyte to a solid support and detecting the ability of the solid support to retain the labeled antibody. If more than one antibody specific for the analyte is found, and there is no steric hinderance preventing more than one antibody binding simultaneously a sandwich-type assay can be employed using one unlabeled specific antibody to capture the antigen, and a second to detect the antigen captured. Alternatively, the kits may comprise panels of antibodies whose recognition pattern for the desired analyte is calibrated. Additionally, a labeled competitive mimotope or mixture may be included to permit the assays to be conducted by competition of the unlabeled analyte in the sample with the labeled mimotope.

Alternatively, the pattern can be reversed and a single antibody characterized with respect to its pattern of binding to several mimotopes, if desired, both with and without competing analyte. This pattern provides, also, a profile characteristic of the analyte. When conducted with a diverse panel of a limited number of mimotopes, for example, about 40-100, preferably about 50-60, with maximal differences in properties, this process can also be used to construct a recognition profile for each of a multiplicity of antibodies. The recognition profiles can be stored in a computer file. Since only a few assays are required for each profile, a large collection of profiles can be recorded. Antibodies likely to bind a novel analyte can be selected electronically by matching the stored recognition profiles for the antibodies against a mimotope homology profile for the novel analyte, as further described below.

The analyte mimotope homology profile will be most easily determined using an inverse image reference antibody set prepared with respect to the mimotope panel. For a 50-mimotope panel, this will comprise 50 antibodies wherein each one of the 50 antibodies binds 10-100 times more strongly to one of the 50 mimotopes than to any of the other 49. Thus, for example, each monoclonal antibody might have a binding affinity of greater than $10^8$ l/mole for the mimotope matching it, but less than $10^6$ l/mole for any of the remaining 49 mimotopes.

The inverse image panel can be obtained using standard monoclonal antibody production techniques by immunizing with the mimotope and screening with the desired mimotope in any conventional screening assay. Monoclonals are selected which have the proper specificity by verifying inability to react with the remaining 49 mimotopes. A convenient preliminary screen, therefore, might involve a competition between a mixture of the 49 labeled noncandidate mimotopes and the unlabeled desired mimotope, in a manner similar to that described for the identification of antibodies in the random panel above.

In a very simple example of application of this concept, a novel analyte that is detected solely by antibody #7 of the inverse image reference panel is evidently displaying some motif strongly analogous to reference mimotope #7, relative to the other 49 mimotopes. An antibody whose stored recognition profile indicates strong binding to mimotope #7, relative to the other 49 mimotopes, thus stands a high probability of recognizing the novel analyte. Similarly, if the novel analyte has equal binding to antibodies #7 and #11 of the inverse image reference panel, and low against all others, then antibodies which recognize mimotopes #7 and #11 equally, and the others negligibly, stand a high likelihood of recognizing the analyte.

More generally, more complex patterns of recognition can also be used. For each antibody in the large collection, a pattern of binding coefficient or immunoreactivity with each of the, say fifty, members of the mimotope panel might be obtained. For example, antibody #664 of the large panel might show a binding coefficient of 50 with mimotope #1, 25 with mimotope #2, 122 with mimotope #3, 10 with mimotope #4, 200 with mimotope #5, and so forth. The resulting 50 point pattern defines the individual antibody.

Because the inverse image reference panel of monoclonal antibodies bears the same relationship to any potential analyte or target antigen as the original 50-mimotope panel bears to the antibodies in the large antibody collection, an arbitrary analyte can be indirectly matched with its closest fit among the large collection of antibodies by testing the analyte against the 50 members of the inverse image antibody set to determine a profile or signature characteristic of the analyte. The profile obtained when each monoclonal antibody in the inverse image set is reacted with the target analyte will match the profile obtained when its ideal partner antibody is tested with the 50-member mimotope panel. In the ideal case, an analyte that will be recognized by antibody #664 will have a reactivity pattern which shows binding coefficients of approximately 50 for Mab #1, 25 for Mab #2, 122 for Mab #3, 10 for Mab #4, 200 for Mab #5, and so forth.

This modification of the screening approach can thus be used to identify a particular antibody from the basal set or from any large set which is reactive with an arbitrary analyte, using complementary smaller sets of diverse mimotopes and inverse image antibodies as a reference index. Each member of the original large antibody set is profiled with respect (for example) to a 50-member diverse mimotope panel, an inverse image antibody set of the 50-member mimotope panel is obtained, and the inverse image antibody panel tested against the potential analyte or antigen to obtain matching profiles.

A useful case for application of this approach is that in which the novel analyte is patient-specific tumor cell-surface antigen, and the antibody collection represents the total accumulated array of anti-tumor monoclonal antibodies, now estimated to be in the many thousands. The array of antitumor antibodies is first typed against a small set of mimotopes to obtain a set of reference profiles. Each cell-surface antigen is profiled with the inverse image of this mimotope set, and the resulting profile compared to stored profiles of the members of the antibody array. The closest match in profile indicates the preferred antibody. The advantages of this approach to characterizing antigens are that: (i) tiny biopsy samples can be typed against a large number of antibodies; (ii) the biopsy sample need not be chemically modified since the detecting tags for measuring binding to the reference panel of antibodies can be attached to the antibodies; and (iii) the candidate array of antibodies can be rapidly and inexpensively surveyed.

E. Improvement of Antibody Characteristics Employing the Immune System

Once a preliminary set of mimotopes has been selected, it can be used to screen large numbers of B-cells for ones with higher affinity/specificity than were available in the first tier screening panel. In the simplest case, the entire resting B-cell repertoire of about $10^7$ cells can be screened on a Fluorescence Activated Cell Sorter using the mimotopes attached to a fluorophore as probe.

Analysis of "maturation" of the normal in vivo immune response suggests that higher affinity clones are not best generated by examining additional basal repertoire B-cells, but by initiating randomization of the hypervariable sequences corresponding to the analyte combining site.

In a straightforward approach, in addition to being useful as a competitive reagent in immunoassay, the selected mimotope or subset is therefore useful as an immunogen to improve antibody specificity and/or affinity. In a sense, this aspect resembles standard in vivo immunization with analyte or antigen except that no supply of antigen is required, and the toxicity of the antigen will be obviated In addition, suppression of and normalization of anti-self T-cell response is available by conjugation of the mimotopes to an appropriate carrier, such as a keyhole limpet hemocyanin (KLH) or tetanus toxoid.

Immunization of a subject mammal with the immunogenic mimotope or subset mixture linked to carrier, thus leads to a supply of B-cells, which can then be immortalized and screened for high affinity and specificity for the particular analyte using, for example, the method employed above, wherein analyte/mimotope competition is diagnostic of specificity and affinity. Alternatively, the B-lymphocytes produced can first be screened, as suggested above, using a fluorescence-activated cell sorter (FACS) by conjugating the mimotope to a fluorescent label thus conducting the reaction used for screening prior to sorting. The identified labeled cells can then be immortalized and rescreened if desired.

The panel of antibodies at this level includes some which are more specific and strongly binding to the mimotopes than were available in the initial screen.

Normally, also, they will be of the IgG rather than the IgM class common in the basal repertoire. Using the immune system of the subject mammal as a somatic mutation mechanism for B-cell differentiation, and selector for the differentiated B-cells to be proliferated gives the resulting panel a far narrower scope in terms of immunoreactive complements, but a much higher specificity and affinity for the complementary analyte upon which focus is centered. To the extent that the mimotopes mimic the relevant features of analyte, the resulting antibodies will have higher specificity and affinity for analyte.

The first aspect of this processing by the immune system, i.e. the differentiation of B-cells to create variation in the contours of the variable regions of the immunoglobulins, can be mimicked using recombinant DNA techniques by creating immunoglobulin—or immunoglobulin fragment-encoding DNAs in a range of modifications from that encoding the candidate antibodies from the original panel. Thus, using known isolation techniques, the DNA encoding the immunoglobulins secreted by the cells chosen from the basal repertoire panel is isolated as the set of starting materials. The sequences contained in the isolated DNAs, which encode the hypervariable regions of the immunoglobulins, can then be altered either randomly or through site-specific mutagenesis to effect modifications in the hypervariable regions of the resulting antibodies. Techniques for identifying and altering the hypervariable regions are known in the art. The mutated DNA is then expressed in yeast or bacteria to obtain the second tier panel, which will provide the scope, but not the selectivity of the immune system generated panel.

Again, with the second tier panel created either by the immune system or by recombinant techniques, an individual antibody with particularly favorable characteristics can be chosen, or, more preferably, a subset is obtained which will provide a panel exhibiting a particular profile with regard to affinity for a given analyte. The employment of the selected panel in general assay procedures is further described below.

F. Use of Antibody Panels in Analysis

The repertoire of antibodies obtained by screening or by immunization with mimotope (or analyte) (whose production can be made permanent by immortalizing the B-cells producing them) can also be used as an identification diagnostic for analyte in test substance. Typically, a convenient small subset will be used, but there is no theoretical reason that a large number cannot be manipulated as described below, when properly formatted. The analyte will exhibit a particular profile of binding which will be characteristic of the analyte.

As set forth above, inverse image panels can be used to characterize either analytes or antibodies. Preferably, the members of the inverse image panels are sufficiently small in number to constitute a practical set, but large enough in number to give a meaningful pattern. Such panels should therefore typically include 30-100 members, preferably about 50 members. The reactivity of the analyte with the monoclonal antibody inverse image reference panel (or the antibody with the mimotope reference panel) can be assessed using a variety of techniques known in the art such as direct or competitive label binding.

Many protocols can be envisioned, but, at a minimum, the patterned, supported panel provides a convenient tool for obtaining one or a plurality of profiles of reactivity for a particular analyte. Because the profiles are so individual, the differences in them can be used to distinguish members of closely related classes of analytes, such as the various types of prostaglandins, various isoenzymes, or closely similar drugs.

Thus, also part of the invention is a panel of 10 to about 10,000, preferably about 50 maximally diverse antibodies, of varying affinity or specificity for analyte, arranged in patterned fashion on a solid support. The solid support can then be used to assess the sample for the presence of analyte by measuring its binding affinity and/or specificity using, for example, serial dilutions of labeled mimotope as competitor, or in a direct assay. A characteristic pattern of such affinity indicates the presence of the analyte, since the pattern obtained is unique to, and characteristic of, a particular substance. The manner of panel presentation described below permits large numbers of members in the panel. The pattern can be read by eye, or can be subjected to scanning techniques and converted to a digital or analog readout.

The invention also includes kits which contain this repertoire of antibodies or mimotopes in a suitable array, optionally along with the appropriate competitive mimotope(s) in a convenient packaging configuration, and along with instructions for conducting the test.

G. Presentation of Panels

It will be noted that many of the steps in the methods of the invention, as well as the kits provided by the invention, require the arrangement of mimotopes or antibody-producing cells in an organized array of individual members or individual pools. Standard methods of obtaining such arrays are available, as set forth above, including the use of microtiter plates and their replicas on nitrocellulose or polystyrene.

A preferred method of preserving this orderly array comprises the use of activated membranes including those which are commercially available or those prepared as described below using derivatized agarose, exemplified by commercially available "NuFix ™" agarose. This material has been used as a support in gels approximately 1.5 mm thick by Shainoff, J. R., et al, *Biotechniques* (1986) 4:120-128. The derivatized agarose provides more binding stability of proteins and peptides than adsorption to polystyrene and nitrocellulose, as covalent bonds are formed. Another aspect of the present invention is an improved method to utilize derivatized agarose as solid support for the needed panels.

In this improvement, rather than the use of derivatized agarose gels, which are difficult to handle and give results which are not completely reproducible, the agarose is impregnated into an inert solid support, such as glass-fiber filter paper. By use of the impregnated solid support, ease of handling and reproducibility are improved greatly.

In order to prepare the supports of the invention, the derivatized agarose, such as NuFix ™ agarose, is dissolved in an appropriate volume of water to about 0.1-0.5%, preferably 0.3%, and boiled before the addition of alkali, such as a final concentration of 0.1M sodium borate. The solid-phase adsorbent, such as glass fiber filter paper of the appropriate size, is immersed in the dissolved agarose, and excess fluid removed. The finished sheets are cooled to permit solidification of the agarose and stored under moist conditions at 4° C.

When ready for use, the sheets of agarose-impregnated paper are equilibrated in fresh sodium borate containing the binding reagent, freshly dissolved sodium cyanoborohydride (1 mg/ml), excess liquid removed, and the samples are plated in a desired pattern on the support. This can be accomplished by a number of commercially available means, including CloneMaster® (Immunsine Corporation), an array of 96 flat-bottom metal rods in the pattern of 96-well microtiter plates, or alternative convenient transferring mechanisms. Transferred materials are allowed to react with the paper for 5-15 min, preferably around 10 min, then fixed in a solution containing buffer and an appropriate protein, such as BSA. The spots are developed using suitable reagent systems appropriate to the material to be detected in the sample.

EXAMPLES

The following examples are intended to illustrate, but not to limit, the invention. Example 1 describes a particular method for providing a panel of antibody-secreting cells which are a subset of the complete B-cell repertoire, representative of that repertoire. Other methods, as outlined in the specification above, could also be used to generate this panel. Also described is a particular method for producing a representative mixture of mimotopes; this, too, could be done by a variety of procedures and using a number of labeling methods, as described above.

Example 2 describes the preparation of the supported antibody panels of the invention.

EXAMPLE 1

Preparation of a Panel of Antibody-Secreting Immortalized Cells

Spleen cells were harvested from 10-week-old male BALB/c mice using standard procedures and placed in a 650 ml flask containing 200 ml complete medium (Iscove's Modified Dulbecco's Medium (IMDM), 10% fetal bovine serum, 0.4 mM 2-mercaptoethanol, 2 mM L-glutamine). Gliding bacterial adjuvant (2 mg) was added to the cells as a polyclonal stimulator, and the stimulated cultures were incubated at 37° C. for four days.

The cells were harvested by centrifugation for 10 min at 1000 rpm and combined with $10^8$ myeloma cells, P3X63AG8.653, which had been similarly harvested in Dulbecco's divalent cation-free PBS and spun for 8 min at 500 rpm. The supernatant was removed and the pellet resuspended in 0.6 ml 50% w/v PEG 4000 (gas chromatography grade) over a 1 min period. The tube containing the resuspended pellet was swirled slowly for 45 sec at 37° C. and allowed to rest for an additional 45 sec period. The cells were repelleted for 3 min at 500 rpm, 15 ml of 37° C. IMDM added slowly to the tube without disturbing the pellet, and then spun for an additional 5 min at 500 rpm.

The supernatant was removed, and the pellet again resuspended in 15 ml complete medium (37° C.) containing 0.4 mM hypoxanthine and $1.6\times10^{-5}$ mole thymidine (complete medium+HT). The suspension was added to 155 ml 37° C. complete medium plus HT, along with 30 ml of the splenic activation medium (the supernatant from the spleen cell harvest). The suspension was poured into a 650 ml flask and incubated for 12-18 hr at 37° C. The suspended cells were fed using macrophages and spleen cells of two BALB/c 10-week-old male mice along with $2\times10^{-7}$ mole aminopterin (A), and the suspension was plated at 200 ul per well in 96-well tissue culture plates for a total of 10 plates. 5-10 clones were obtained per well. Thus, over 5000 antibody-producing cells were obtained from the one initial activated spleen. The colonies may be further separated into individual cell lines, or may be used as pools for initial screening.

EXAMPLE 2

Preparation of Panels on Supported Agarose

NuFix ™ agarose was dissolved at slightly more than 0.3% in water at 70° C. for 10 min followed by boiling for 10 min, as described by the manufacturer. One-tenth volume of 0.1M sodium borate, pH 9, was added, and the solution poured into pans sitting in a 55° C. water bath. Sheets of glass fiber filter paper (Schleicher and Scheull) cut to $3''\times5''$ were dipped into the agarose and excess fluid removed by blotting on absorbent paper. The sheets were placed on wax paper and refrigerated for 10 min to permit the agarose to solidify; the sheets were stored in a moist box at 4° C.

For use, the impregnated paper was equilibrated for 5 min in 0.1M sodium borate, pH 9, containing 1 mg/ml sodium cyanoborohydride. Excess liquid was drained and blotted, and the sheet was placed on plastic wrap. One microliter samples from each well of the 96-well plate, with or without growing murine cells, were transferred to the paper in a standard 96-dot pattern, and the transferred dots of culture plate media allowed to react with the paper for 10 min. To block excess binding sites, the sheet was then soaked in a solution of 0.1M Tris-HCl, pH 8, 0.1M NaCl containing 1% w/v bovine serum albumin. After removing the liquid, 5 ml peroxidase-coupled goat anti-mouse serum (Zymed), diluted 1:3000 in the same buffer, was pipetted onto the sheet and the sheet incubated at room temperature for 15 min, or the reagent was applied by blotting against filter paper permeated with the reagent. Unbound antibody was removed by suction, and the paper was washed for 5-10 min with multiple changes of phosphate-buffered saline containing 0.1% BSA.

The bound peroxidase was visualized using 10 mg/ml tetramethylbenzidine in 50% methanol, 50% citric acid, to which hydrogen peroxide had been added at a final concentration of 0.1%. The results were recorded with a reflection densitometer or by photography.

FIG. 1 shows the results of serial dilutions of a hybridoma culture across successive rows of the plate. The variation in intensity is clearly seen.

The panels of test materials can be read manually or using quantitative detection methods. For example, the arranged panel may be read in a specialized apparatus designed to digitize the signal, such as a fluorescent signal, from each of the individual spots and outputting it in computer-readable format. Thus, a quantitative measure may be had of each individual spot.

Particular configurations of the panel which are useful in the process of the invention include cards of small dimension, for example, $3''\times3''$, containing 100 rows and 100 columns of dots. This total array of 10,000 separate individual antibodies, or pools of antibodies, leads to characteristic patterns of reactivity with particular analytes.

EXAMPLE 3

Synthesis of a Diverse Mimotope Panel

Figure 4:
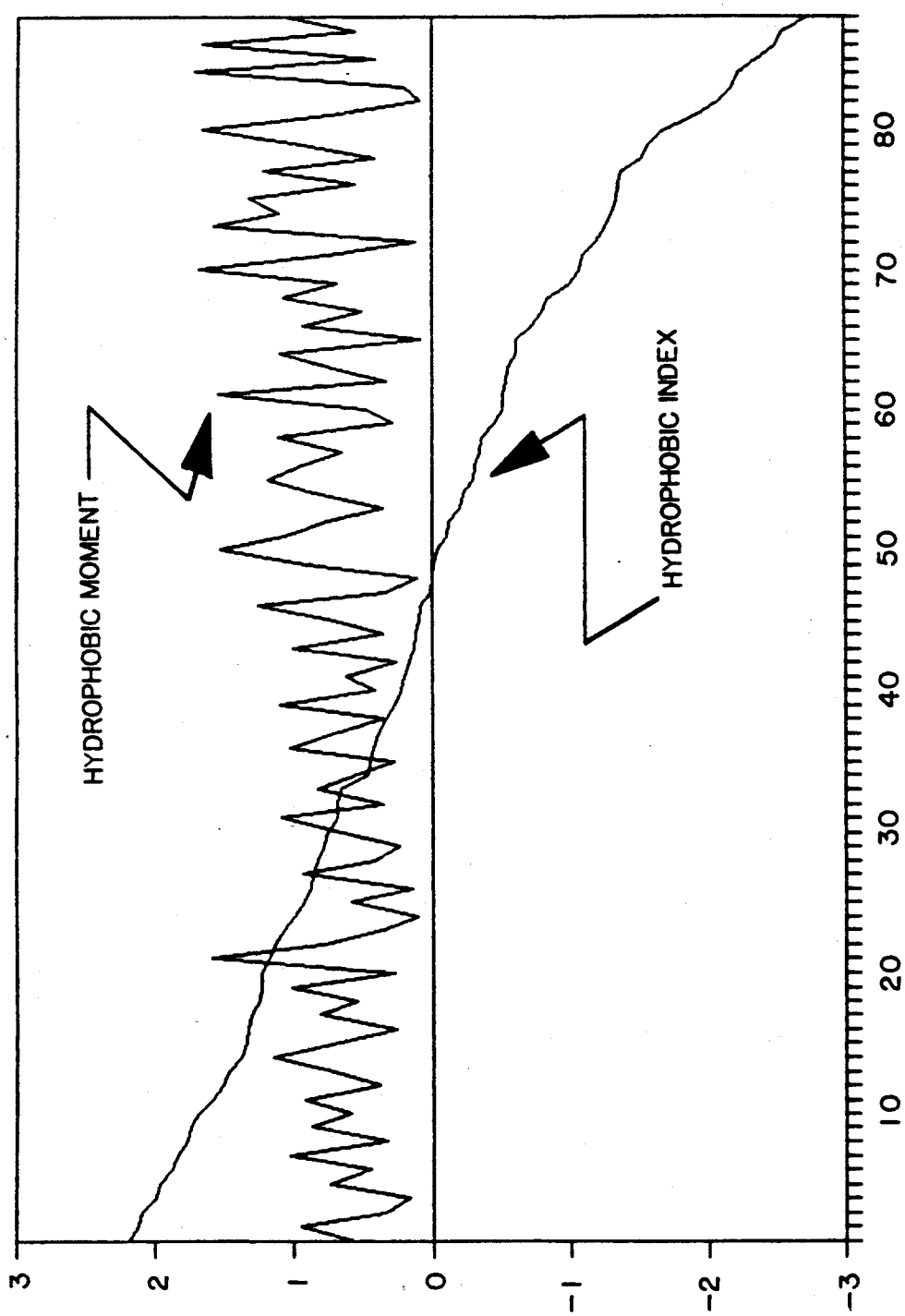
FIG. 4 shows the range of hi and hm across the peptides of FIG. 3.

A panel of 88 pentapeptides was designed on the basis of decreasing hydrophobicity and periodic variation of hydrophobic moment. FIG. 3 shows the list of pentapeptides synthesized numbered 1–88; FIG. 4 shows the hydrophobic index and the hydrophobic moments across this panel.

The panel is synthesized using the method of Geysen, H. M., et al, *Proc Natl Acad Sci USA* (1984) (supra), which uses lots of 96 pins. The remaining eight polyethylene pins are used for controls on the synthesis to be analyzed by amino acid analysis.

The mimotopes of the panel are then mixed, labeled with 125-I using the Bolton-Hunter reagent, as described above, and tested with the individual members of the basal antibody repertoire in microtiter wells. Nearly uniform binding to all antibody members of the repertoire is found. The test is then repeated with the addition of a defined amount of analyte to the mixture in the microtiter wells. A small number of wells show greatly decreased labeling. These antibodies represent the successful result of an initial screen for those which preferentially bind analyte.

EXAMPLE 4

Figure 6:
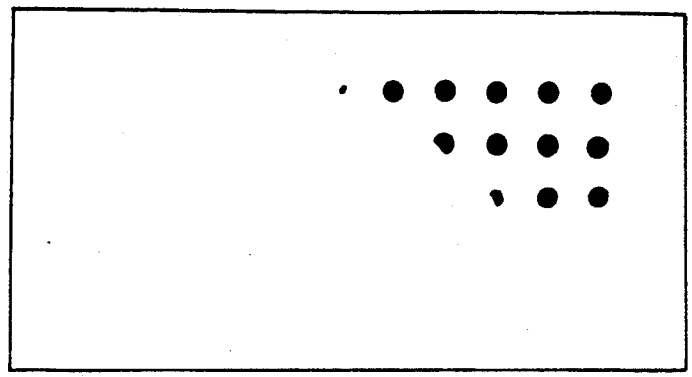
FIG. 6 shows a competitive assay between two mimotopes.

The effectiveness of labeled mimotope as the competitor for nonidentical analyte in screening antibodies is seen in FIG. 6. Two different monoclonal antibodies were applied in duplicate rows of 12 spots per row on a filter paper substrate. In FIG. 6, rows 1 and 2 were spotted with Mab 33-6, rows 3 and 4 were spotted with Mab 9-7-9, and row 5 serves as a control with no antibody. Bovine serum albumin was applied to all spots to block excess binding sites. Spots of labeled peptide/mimotope, MB4-FITC (MB4=Cys-Asn-Try-Ser-Lys-Tyr*-Trp-Tyr-Leu- Glu-His-Ala-Lys) in columns 2–11 of the panel were applied at a set concentration of $2 \times 10^{-5}$M. Columns 2–11 also contain unlabeled competitor peptide/analyte MB3 (MB3=Cys-Asn-Tyr-Ser-Lys-Phe*-Trp-Tyr-Leu-Glu-His-Ala-Ile-Ser) (*=difference in amino acid residue) in successively lower dilutions beginning with a concentration of $4 \times 10^{-4}$M in column 2 and successive 1:1 dilutions in columns 3–11. The resulting substrate was then incubated and washed (Bio-Dot apparatus).

FIG. 6 shows that with respect to each Mab, the labeled MB4 peptide successfully competed with the unlabeled competitor peptide MB3 as the MB3 competitor was diluted, yielding a characteristic pattern on the panel for each of the two Mabs tested.

EXAMPLE 5

The ability of even a small number of diverse mimotopes to contain a suitable peptide for binding to an arbitrarily chosen antibody is demonstrated in this example. FIG. 7 shows the amino acid sequences for 24 nonapeptides synthesized according to the method of Houghten (supra). These peptides were designed to show high diversity in hydrophobic moment and hydrophobic index, as well as charge distribution and size.

Sixteen of these peptides were tested for ability to bind the murine antibody Mab 33-6, arbitrarily chosen, and known to bind to the peptides MB3 and MB4 as described in Example 4. Binding was tested using the commercially available Bio-Rad Dot-Blot apparatus, which provides an activated paper or nitrocellulose substrate with a patterned overlay which defines rows and columns of test dot sites on the substrate. The results are shown in FIG. 8.

Briefly, the test was conducted by pipetting 1 λ of the peptide solution to be tested onto a designated spot, in this case, onto triplicate spots. The substrate was blocked with casein or BSA, and then the antibody applied by pressing the substrate onto a Saran wrap support onto which 25 λ of solution containing 1 μg/ml of Mab 33-6 had been applied. The substrate was incubated at room temperature in contact with the antibody solution for about 1 hr, and then removed and washed in buffer. The substrate was then incubated with labeled goat antimouse Ig which had been labeled with horseradish peroxidase, and the presence of label detected by standard means.

Figure 8:
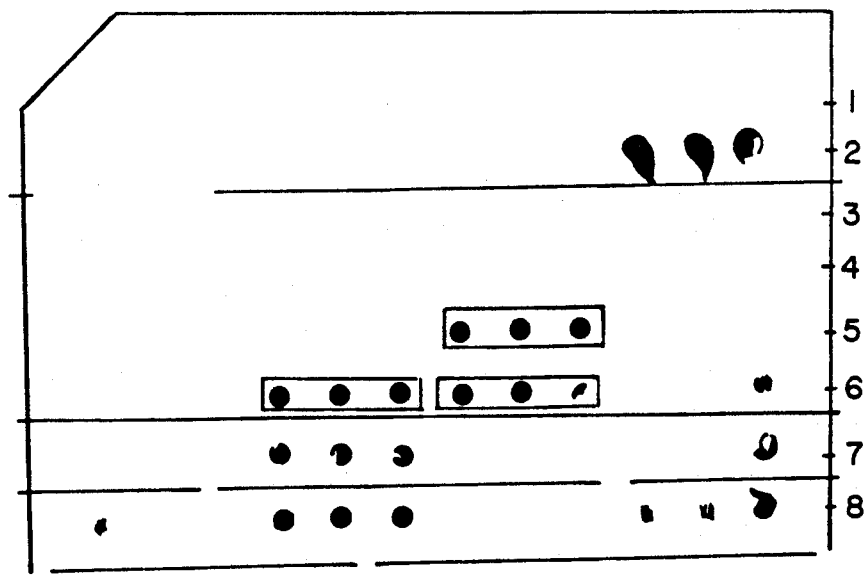
FIG. 8 shows the results of an assay testing the binding of 16 members of the set of FIG. 7 to an arbitrary antibody.

As shown in FIG. 8, the last three dots in row 2 of the actuated substrate contain the peptide MB3 which is known to bind to Mab 33-6 based on homology of the peptide to the sequence of the known epitope. Rows 3–6 each contain 4 triplicate samples of different peptides 1–16 of the diverse set shown in FIG. 7. Rows 7 and 8 contain additional controls. The results in FIG. 8 show that 3 of the 16 peptides tested successfully bound Mab 33-6. A similar assay using Mab 9-7-9 instead of Mab 33-6 yielded one peptide capable of binding this antibody of the 16 tested.

I claim:
1. A method to identify antibodies reactive with a desired analyte which method comprises:
   a) reacting a panel containing antibodies secreted by a multiplicity of individual colonies of immortalized cells which secrete antibodies representative of the resting B-cell repertoire of a mammal with a mixture of mimotopes whose members are representative of a diverse set of 3-dimensional charge and space contours in competition with said analyte; and
   b) identifying from the panel a smaller subset of antibodies secreted by at least one colony producing antibodies for which analyte successfully competes with the mimotope mixture.

2. The method of claim 1 wherein the panel of antibodies secreted by a multiplicity of colonies of immortalized cells is a panel of antibodies secreted by colonies of immortalized randomly stimulated antibody-producing cells.

3. The method of claim 1 wherein the panel of antibodies secreted by a multiplicity of colonies of immortalized cells is a panel of antibodies secreted by colonies of recombinant host cells transfected with DNA encoding a multiplicity of antibodies.

4. A kit useful for performing the method of claim 1 which comprises a panel of antibodies secreted by a multiplicity of individual colonies of immortalized cells which secrete antibodies representative of the basal repertoire and a mixture of diverse mimotopes representative of a diverse set of 3-dimensional charge and space contours.

5. The kit of claim 4 wherein the panel of antibodies secreted by colonies of immortalized cells is a panel of antibodies secreted by colonies of immortalized randomly stimulated antibody-producing cells.

6. The kit of claim 4 wherein the panel of antibodies secreted by colonies of immortalized cells is a panel of antibodies secreted by colonies of recombinant host cells transfected with DNA encoding a multiplicity of antibodies.

7. The kit of claim 4 wherein the mimotope mixture is a mixture of randomly generated peptides.

8. The kit of claim 4 wherein the mimotope mixture is a mixture of peptides of designed diversity.

9. A kit for detection of an individual analyte which comprises a solid support upon which is bound, in an orderly array, a panel of a multiplicity of immunoglobulins which react in differing degrees with the analyte, said differences providing a characteristic profile of the analyte which further includes a mixture of labeled mimotopes competitive with the analyte.

10. A panel of antibodies which is an inverse image of a panel of mimotopes wherein each mimotope comprises a peptide of 3-10 amino acids, wherein the peptides in the panel are maximally diverse with respect to hydrophobic index and pI.

11. The panel of claim 10 wherein the peptides of the mixture are additionally maximally diverse with respect to hydrophobic moment.

12. The panel of claim 10 wherein the peptides of the mixture are additionally maximally diverse with respect to dipole moment.

13. The panel of claim 10 wherein the peptides of the mixture are additionally maximally diverse with respect to corrugation factor.

14. A method of characterizing a particular analyte, comprising:
   (a) successively reacting each member of a panel of diverse antibodies with separate labeled mimotopes that are individual members of a set of mimotopes, said set representing a diverse set of three-dimensional contours to obtain a binding signal profile for each mimotope of the diverse mimotope set with respect to each antibody of the panel;
   (b) adding the binding signals for all the mimotopes of the diverse set for each antibody of the panel;
   (c) normalizing the binding signals of step (b);
   (d) competitively reacting unlabeled analyte which is to be characterized and a mixture containing the diverse set of labeled mimotopes from step (a) with each antibody of the panel; and
   (e) determining the amount of reduction in comparison to the normalized binding signals of said mixed labeled mimotopes for each antibody of the panel resulting from successful competition of the analyte for the panel antibody to obtain a pattern of reactivity for said analyte with the panel.

15. A method to match an analyte to an antibody contained in a large candidate antibody set which is immunoreactive with said analyte, which method comprises
   (a) constructing a panel of antibodies which is an inverse image of a maximally diverse set of mimotopes in that each antibody binds to one of said mimotopes with a binding constant at least 20 times greater than that with any of the other mimotopes in the set;
   (b) preparing a profile of the degree of binding of the analyte to the members of the inverse image antibody panel of (a);
   (c) preparing a profile of the degree of binding of each of the antibodies contained in said large candidate set by each of the mimotopes in said diverse set; and
   (d) comparing the mimotope-binding profile of each member of the large candidate set of antibodies prepared in (c) with the inverse image binding profile of the analyte prepared in (b), whereby said analyte is matched to an antibody which provides a mimotope binding profile which matches said inverse image binding profile.

16. A method to match an analyte to an antibody in a candidate set of antibodies immunoreactive with it, which method comprises
   (a) reacting said analyte with an inverse image panel which has been constructed by preparing a panel of antibodies which is an inverse image of a maximally diverse set of mimotopes in which each antibody binds to one of said mimotopes with a binding constant at least 20 times greater than that with any of the other mimotopes in the set; and
   (b) comparing the pattern of reactivity of the analyte with said inverse image panel with the predetermined pattern of reactivity of each antibody of the candidate set with said mimotope set, whereby said analyte is matched to an antibody which provides a pattern of reactivity with said mimotope set which matches the pattern of reactivity of the analyte with the inverse image panel.

17. The method of claim 16 wherein said candidate antibodies are monoclonal antibodies.

18. The method of claim 16 wherein said inverse image antibody panel comprises approximately 20 antibodies.

19. A method of characterizing a particular analyte, comprising:
   competitively reacting unlabeled analyte which is to be characterized and a mixture containing a diverse set of labeled mimotopes, representing a diverse set of three-dimensional contours, with each antibody of a diverse antibody panel and determining the amount of reduction the normalized binding signals of said mixed labeled mimotopes for each antibody of the panel resulting from successful competition of the analyte for the panel antibody, thus obtaining a binding profile with said antibody panel characteristic of said analyte, wherein
   the binding signals for each mimotope of said diverse set have been normalized by successively reacting members of said panel of diverse antibodies with separate labeled mimotopes that are individual members of said diverse set of mimotopes to obtain a binding profile for each mimotope of the diverse mimotope set with respect to each antibody of the panel;
   adding the binding signals for all the mimotopes of the diverse set for each antibody of the panel; and
   normalizing the added binding signals.

* * * * *

UNITED STATES PATENT AND TRADEMARK OFFICE
CERTIFICATE OF CORRECTION

PATENT NO. : 5,217,869
DATED : June 8, 1993
INVENTOR(S) : Lawrence M. Kauvar

It is certified that error appears in the above-indentified patent and that said Letters Patent is hereby corrected as shown below:

In the Drawings:

Please delete Figure 6.

Change the label on Figure 2B to read --335 Mabs AGAINST PHAGE f1--.

Change the label on Figure 2C to read --335 Mabs AGAINST KLH--.

Column 5, lines 25-26, please delete the entire sentence "FIG. 6 shows a competitive assay between two mimotopes."

Column 27, lines 23-24, please delete "is seen in FIG. 6." and substitute therefor --was tested on filter paper substrate.--

Column 27, line 26, please delete "In FIG. 6," and change "rows" to --Rows--

Column 27, line 42, please delete "FIG. 6 shows that" and change "with" to --With--.

Signed and Sealed this

Nineteenth Day of December, 1995

*Attest:*

BRUCE LEHMAN

*Attesting Officer*  *Commissioner of Patents and Trademarks*